US009446193B2

(12) United States Patent
Geipel et al.

(10) Patent No.: US 9,446,193 B2
(45) Date of Patent: Sep. 20, 2016

(54) DOSING UNIT FOR AN INFUSION PUMP DEVICE

(71) Applicant: Roche Diagnostics International AG, Rotkreuz (CH)

(72) Inventors: Andreas Geipel, Heddesheim (DE); Joerg Dogwiler, Bergdietikon (CH); Ulrich Haueter, Grosshoechstetten (CH); Simon Scheurer, Bern (CH); Rudolf Zihlmann, Langnau (CH); David Teutsch, Schuepfen (CH); Florian Kuehni, Bern (CH); Reto Schaltegger, Muenchenbuchsee (CH)

(73) Assignee: Roche Diagnostics International AG, Rotkreutz (CH)

( * ) Notice: Subject to any disclaimer, the term of this patent is extended or adjusted under 35 U.S.C. 154(b) by 0 days.

(21) Appl. No.: 14/049,528

(22) Filed: Oct. 9, 2013

(65) Prior Publication Data
US 2014/0039396 A1    Feb. 6, 2014

Related U.S. Application Data

(63) Continuation of application No. PCT/EP2012/056538, filed on Apr. 11, 2012.

(30) Foreign Application Priority Data

Apr. 12, 2011  (EP) .................................... 11161979

(51) Int. Cl.
*A61M 5/172*    (2006.01)
*A61M 5/142*    (2006.01)
(Continued)

(52) U.S. Cl.
CPC ......... *A61M 5/172* (2013.01); *A61M 5/14216* (2013.01); *A61M 5/14244* (2013.01);
(Continued)

(58) Field of Classification Search
CPC ................... A61M 5/14216; A61M 5/16809; A61M 5/172; A61M 5/31528; A61M 2205/3306; A61M 2205/3396
USPC ........ 604/154, 155, 207, 211, 218, 224, 236
See application file for complete search history.

(56) References Cited

U.S. PATENT DOCUMENTS 3,756,456 A    9/1973 Georgi
RE29,495 E    12/1977 Georgi
(Continued)

FOREIGN PATENT DOCUMENTS

DE    3515624 A1    11/1986
EP    0025575 A1    9/1980
(Continued)

*Primary Examiner* — Kami A Bosworth
*Assistant Examiner* — Nilay Shah
(74) *Attorney, Agent, or Firm* — Roche Diagnostics International AG

(57) ABSTRACT

A dosing unit for an ambulatory infusion pump device is presented. The dosing unit comprises a cylinder pump with a cylinder and a piston arranged in the cylinder. The piston has a shaft with a first threaded segment interacting with a threaded portion of the cylinder and can be displaced along a longitudinal axis of the cylinder by rotating the piston in regard to the cylinder around the axis. Furthermore, the piston allows for the relative or absolute determination of the longitudinal and/or rotational displacement of the piston in regard to the cylinder. In one embodiment, the piston shaft comprises a second segment provided with optically detectable markings that allow the monitoring of the longitudinal and/or rotational displacement of the piston in regard to the cylinder.

15 Claims, 9 Drawing Sheets

(51) Int. Cl.
  *A61M 5/168* (2006.01)
  *A61M 5/36* (2006.01)
  *A61M 5/315* (2006.01)
  *A61M 5/14* (2006.01)

(52) U.S. Cl.
  CPC ......... *A61M5/16809* (2013.01); *A61M 5/365* (2013.01); *A61M 5/31511* (2013.01); *A61M 2005/1402* (2013.01); *A61M 2005/14208* (2013.01); *A61M 2005/14264* (2013.01); *A61M 2005/16868* (2013.01); *A61M 2205/3306* (2013.01); *A61M 2205/3355* (2013.01); *A61M 2205/3365* (2013.01); *A61M 2205/3396* (2013.01)

(56) References Cited

U.S. PATENT DOCUMENTS

| | | | |
|---|---|---|---|
| 4,345,483 | A | 8/1982 | Paletta et al. |
| 5,935,105 | A | 8/1999 | Manning et al. |
| 6,113,578 | A * | 9/2000 | Brown .......... 604/207 |
| 6,416,293 | B1 | 7/2002 | Bouchard et al. |
| 7,955,302 | B2 | 6/2011 | Haueter et al. |
| 8,277,423 | B2 | 10/2012 | Haueter et al. |
| 8,277,434 | B2 | 10/2012 | Haueter et al. |
| 2004/0044332 | A1 | 3/2004 | Stergiopulos |
| 2004/0135078 | A1* | 7/2004 | Mandro et al. .......... 250/231.13 |
| 2006/0224123 | A1* | 10/2006 | Friedli et al. .......... 604/207 |
| 2007/0053672 | A1 | 3/2007 | Westerweck et al. |
| 2008/0077081 | A1 | 3/2008 | Mounce et al. |
| 2008/0086111 | A1 | 4/2008 | Cowan et al. |
| 2008/0156476 | A1 | 7/2008 | Smisson et al. |
| 2011/0043357 | A1 | 2/2011 | Peatfield et al. |
| 2011/0190694 | A1* | 8/2011 | Lanier et al. .......... 604/67 |
| 2011/0213329 | A1* | 9/2011 | Yodfat et al. .......... 604/500 |
| 2012/0268741 | A1* | 10/2012 | Pommereau et al. .......... 356/343 |

FOREIGN PATENT DOCUMENTS

| | | |
|---|---|---|
| EP | 1736738 A2 | 12/2006 |
| EP | 1754505 A1 | 2/2007 |
| EP | 1970677 A1 | 9/2008 |
| EP | 2163273 A1 | 3/2010 |
| EP | 2201973 A1 | 6/2010 |
| EP | 2295096 A1 | 3/2011 |
| FR | 2185790 A1 | 1/1974 |
| WO | 98/03215 A1 | 1/1998 |
| WO | 01/83008 A1 | 11/2001 |
| WO | 02/13890 A1 | 2/2002 |
| WO | 2007/077255 A2 | 7/2007 |
| WO | 2007/133942 A2 | 11/2007 |
| WO | 2009/044221 A1 | 4/2009 |
| WO | 2010055504 A1 | 5/2010 |
| WO | 2011/032960 A1 | 3/2011 |

* cited by examiner (a)

Prior Art (b)

Prior Art

| $t_{admin,i}$ [min] | $V_{dose,i}$ [mm] | $V_{air,i}$ [IU] |
|---|---|---|
| 3 | 4 | 0 |
| 3 | 4 | 0 |
| 3 | 4 | 0.01 |
| 3 | 4 | 0.02 |
| (…) | (…) | (…) |
| 3 | 4 | 0 |
| 3 | 4 | 0 |
| 1 | 500 | 0.08 |
| 2 | 4 | 0 |
| 3 | 4 | 0.01 |
| 3 | 4 | 0 |
| 3 | 6 | 0 |
| (…) | (…) | (…) |
| 3 | 6 | 0.02 |
| 3 | 6 | 0.01 |
| 3 | 6 | 0 |
| 3 | 6 | 0.03 |
| 3 | 6 | 0.03 |
| (…) | (…) | (…) |
| 3 | 6 | 0 |
| 3 | 6 | 0.01 |

- newest data set → (top row)
- $V_{Down}$
- 24 h
- 1st basal rate
- bolus (row with 1, 500, 0.08)
- 2nd basal rate
- oldest data set → (bottom row)

Fig. 9

| $t_{admin,i}$ [min] | $V_{dose,i}$ [mm] | $V_{air,i}$ [IU] |
|---|---|---|
| 3 | 4 | 0 |
| 3 | 4 | 0 |
| 3 | 4 | 0.01 |
| 3 | 4 | 0.02 |
| (…) | (…) | (…) |
| 3 | 4 | 0 |
| 1 | 600 | 0.09 |
| 2 | 4 | 0.01 |
| 2 | 4 | 0 |
| 3 | 6 | 0.01 |
| 3 | 6 | 0 |
| 3 | 6 | 0 |
| (…) | (…) | (…) |
| 3 | 6 | 0.02 |
| 3 | 6 | 0.01 |
| 1 | 400 | 0.05 |
| 2 | 6 | 0 |
| 3 | 6 | 0.03 |
| 3 | 6 | 0.01 |
| 3 | 6 | 0 |
| 3 | 4 | 0 |
| 3 | 4 | 0.02 |
| (…) | (…) | (…) |
| 1 | 500 | 0.07 |
| 2 | 4 | 0 |
| 3 | 4 | 0.01 | newest data set → (top)
$V_{Down}$ (upper bracket)
24 h (lower bracket)
oldest data set → (bottom)

DOSING UNIT FOR AN INFUSION PUMP DEVICE

CROSS-REFERENCE TO RELATED APPLICATIONS

This application is a continuation of PCT/EP2012/056538, filed Apr. 11, 2012, which is based on and claims priority to EP 11161979.7, filed Apr. 12, 2011, which is hereby incorporated by reference.

BACKGROUND

The present disclosure generally relates to dosing units for infusion pump devices, infusion pump devices with such dosing units, and methods for operating such infusion pump devices.

Devices for the automated release of liquid medicaments are normally used with patients who have a continuous and, in the course of the day, varying need of a liquid medicine administered by infusion. Specific applications are, for example, certain pain therapies, cancer therapies and the treatment of diabetes mellitus, in which computer controlled infusion pump devices are used. Such devices are particularly useful for ambulatory therapy and are generally carried attached on or near the body of a patient. The medicine reservoir often comprises medicine supply sufficient for one or several days. The liquid medicament is supplied to the patient's body from the medicine reservoir through an infusion cannula or an injection needle.

Ambulatory infusion pump devices are typically of the syringe driver type as schematically described in FIG. 1(a). The liquid medicament to be administered to the patient 32 is stored in a cylinder 14 of the dosing unit 10, comprising the complete reservoir 11 of liquid medicament of the infusion pump device. The liquid medicament is conveyed to the body of the patient 32 by unidirectionally displacing a piston 16 within the cylinder via a piston shaft 18 or threaded spindle. An outlet 25 is fluidly connected 26 to infusion tubing 28, which on its other end is fluidly connected to an infusion site interface 30 attached to the body. For safety reasons, it is generally preferred to regularly replace any parts that come into contact with liquid medicament, such as for example the infusion tubing. The reservoir is, in most cases, a single use cartridge that may be provided prefilled, or may be provided empty and is filled by the user.

A number of drawbacks of such syringe-type pump designs are known in the art. In particular, such pump devices have a limited precision, because very small volumes, typically in the nanoliter range, are pumped out of a cartridge having an overall volume in the range of milliliters. To achieve precise dosing of the liquid medicament, it is necessary to very precisely displace the piston. Even small deviations can lead to over dosing or under dosing, and the forces needed to actuate the piston are comparably high due to the friction between the walls of the glass cartridge and the sealing of the piston and the material hysteresis of the sealing. This leads to demanding requirements for the drive system and the mechanical parts involved, as well as the control unit of the pump. As a consequence, such infusion pump devices are expensive.

Another problem is the lower limit of the length of such an infusion pump device. The complete supply of liquid medicament has to be stored in the cartridge acting as the pump cylinder. The cross-sectional area of the piston has to be below a certain limit, for precision reasons and in order to limit the device thickness, which is known to be a particularly critical dimension with respect to comfort and discreetness during application. The minimum overall length of the device is then essentially given by the resulting minimum length of the cylinder, which is detrimental to the provision of compact infusion pumps. Particularly in self-administration of medicaments, for example insulin, the patients using the medicament in question and administering it themselves by an infusion pump are increasingly emphasizing convenience and discretion which restricts the acceptable size and weight of such devices so not be evident through clothing and to be carried as comfortably as possible.

In an alternative approach, a separate dosing unit is provided downstream from the liquid medicament reservoir. Since the primary reservoir does not have to fulfill additional functions, its dimensions can be optimized in view of the compactness of the infusion pump device. Such a dosing unit may for example comprise a micro piston pump with small dimensions that retrieves liquid medicament from the larger primary reservoir, e.g., a collapsible reservoir, and conveys the liquid medicament to the body of the patient. Such pumps are generally full-stroke pumps, where the cavity of a membrane pump or the cylinder of a piston pump is always completely emptied. Hence, the inner volume of the pump must correspond to the smallest volume increment that has to be delivered, typically in the nanoliter range. While several designs for such dosing units are known in the art, they are rather complex, expensive and critical with respect to large scale manufacture, since they integrate a number of functional components, in particular metering components and valves and are frequently made from materials which are costly and/or critical in production and processing, such as silicon. Since it is preferable to realize all parts that come into contact with the liquid medicament, including the pump, as disposable elements that are replaced after a certain time, such pump designs are costly. Thus advantageously all expensive parts of a dosing unit should be reusable while the disposable parts should be producible at lower costs.

One implantable infusion pump device, with an primary reservoir in the form of an elastic bellow, a conduit fluidly connecting the conduit to a variable-volume chamber in the form of an elastic bellow, a valve with which the conduit can be opened and closed, and a downstream catheter fluidly connecting the variable-volume chamber with the infusion site is known. The volume of the variable-volume chamber is considerably smaller than the volume of the primary reservoir. Two limiters are placed in such a way as to limit the variation in volume of the variable-volume chamber, between a lower volume limit and an upper volume limit. In a first step, the elastic reservoir is filled by a syringe, the valve being closed. Starting from a certain degree of extension of the elastic reservoir, the restoring force of the latter is such that the liquid can be expelled into the conduit. When the valve is open, the liquid is conveyed toward the variable-volume chamber, driven by the pressure differential in the primary reservoir. As soon as the upper volume limit of the variable-volume chamber is reached, the valve closes and the liquid is conveyed by the restoring force of the elastic variable-volume chamber into the downstream catheter and toward the site to be treated. When the variable-volume chamber reaches the lower volume limit, liquid is no longer expelled from it. At the end of a time interval, determined as a function of the desired dosage rate, the valve opens again and the process as described above is continuously repeated. In other words, the primary reservoir of the device acts as a spring force driven syringe pump with constant dosage rate. The administration rate is controlled by the time intervals between temporarily opening the valve, each corresponding to a full stroke of the spring force driven secondary piston pump in the form of the elastic variable-volume chamber, and the positions of the two limiters, which regulate the volume per stroke.

Although the dosage precision is said to be high in such a device, this precision is based on a statistical average. The volume of single administered portions cannot be adjusted, only the average administration rate can be changed. As a result such a device cannot be used for dosage regimes as necessary for the treatment of diabetes mellitus, in which the administered dosage of each single portion of insulin should be adjustable to the current need of the patient.

The use of such a device is even potentially dangerous, particularly when using highly potent drugs such as insulin. Although it is suggested to use controllable valves in both conduits in order to avoid the known problem of the temporary bypass between the primary reservoir and the catheter during filling of the variable-volume chamber, a malfunction of the valves can lead to an unrestricted and uncontrolled flow of liquid medicament from the primary reservoir directly to the catheter. The possibility of such an event has to be avoided at all cost.

In yet another approach, the cylinder of the piston pump of the dosing unit acts as a secondary reservoir and can hold an intermediate amount of liquid medicament. The pump retrieves liquid medicament from the primary reservoir and conveys the medicament in variable doses. This compromise allows reducing the overall device dimensions while at the same time doses of variable quantities can be provided.

A device following such an approach has a flexible secondary reservoir with an adjustable volume that is fluidly connected by a first conduit to a flexible primary reservoir and by a second conduit to an infusion catheter. The volume of the second reservoir, e.g., 100 µl, is chosen between the volume of the primary reservoir, e.g., 10 ml, and the volume of the smallest intended dosage portion, e.g., 1 µl. A valve is arranged in each conduit for controlling the correct flow of liquids during the filling of the secondary reservoir and during the dosing. The valves are either check valves, which allow the flow of liquid only in the foreseen direction, from the primary reservoir to the secondary reservoir during filling and from the secondary reservoir to the catheter during dosing, or electrically controlled valves that are opened and closed as necessary for achieving such a function.

The use of such a device is again potentially dangerous, particularly when using highly potent drugs such as insulin. When check valves are applied, any over pressure in the primary reservoir will directly lead to an unrestricted and uncontrolled flow of liquid medicament from the primary reservoir via the second chamber to the infusion site. The same is the case if for some reason electrically controlled valves malfunction and are both open at the same time. Since this problem is known, the pressure inside the primary reservoir must in no case be higher than environmental pressure. However, obviously such a precondition for a save operation of the device cannot be guaranteed. Particularly when for some reason a certain amount of air is present in the primary reservoir, any increase of environmental temperature of decrease of environmental pressure will inevitably lead to an overpressure in the primary reservoir.

One embodiment of such a type of infusion pump device is schematically depicted in FIG. 1(b). A 4/3 or 3/3 way valve 35 is arranged at a front end of the cylinder 14 of the dosing unit 12. The valve is realized as a rotatable cylinder head acting as a valve member, which interacts with a fixed cylinder tube acting as the valve seat. A piston 16 in the cylinder of the dosing unit can be bidirectionally displaced along the cylinder axis by a drive system 20. During the refill mode, when the dosing unit retracts the piston and sucks liquid medicament from the primary reservoir 11 into the cylinder 14, an inlet conduit 24 fluidly connected to the primary reservoir is fluidly connected to the cylinder and an outlet conduit 25 fluidly connected 26 to the infusing tubing 28 is disconnected from the dosing unit. During the pumping mode, when liquid medicament is conveyed from the secondary reservoir 15 in the cylinder of the dosing unit to the subcutaneous tissue of the patient 32, the cylinder 14 of the dosing unit is fluidly connected to the outlet conduit 25 establishing a fluid connection to the body of the patient while the inlet conduit 24 is disconnected from the dosing unit.

Alternatively, a rotatable cylinder can act as the valve member mounted in a fixed valve seat. An embodiment of the latter variant is where the actuator of the piston indirectly actuates the valve member by rotating the cylinder frictionally connected to the piston.

For precise metering, it is necessary to either use a pump motor that can be very precisely controlled, for example a stepper motor, or to monitor the actual position of the piston.

One method discloses monitoring the position of a displaceable stopper in an insulin ampoule. In one approach, the displaceable stopper is equipped with markers, e.g., visual markers, that can be detected by sensors arranged along the ampoule. In order to precisely determine the position of the stopper, a large number of sensors are necessary. The cylinder wall has to be at least partially transparent so that the sensors can see the visual markers.

One known syringe-like injection pen device has a piston rod provided with optical markings, namely numbers, which can be visually detected by a user through an aperture in the housing. By reading the number in the aperture, the user can monitor the position of the piston in the syringe, for determining the administered or remaining dose. For an automated system, this approach is not precise enough.

One known infusion pump device with a cylinder pump has a longitudinally displaceable piston with a split piston shaft that connects the piston head with a threaded nut. The piston cannot rotate. The threaded nut interacts with a rotating threaded drive shaft, thereby translating the rotation of the drive shaft into a linear displacement of the piston head. One or more detectable features such as magnetic or optical markers can be arranged on the piston shaft, which can be detected by a corresponding sensor for determining the linear position of the marker and thus of the piston head. The precision of the position determination is restricted by the precision of the determination of the linear position of the marker.

One known cylinder pump discloses a wheel interacting with the piston shaft during the linear displacement of the piston. The linear displacement is translated into a rotation of the wheel and further to a rotation of a second wheel with a multitude of radial lines. This wheel is illuminated through a transparent plate that is also provided with a multitude of radial lines. A single sensor detects the impinging light. In addition to the complex construction of such a device, with a multitude of moving parts, the achievable precision is inherently reduced by frictional slip between wheel and piston shaft.

In a worst case pump failure scenario, the whole content of the reservoir can be inadvertently administered because of continuous and unintended operation of a pump unit, e.g., due to a fault in the drive control circuitry. Although, the maximum dosing volume in the secondary reservoir is considerably smaller than the complete content of a cartridge of a conventional syringe pump, for example by a factor of 25, the liquid medicaments that are administered by liquid infusion pump devices are generally highly effective and the inadvertent administration of the complete secondary reservoir is undesirable.

Another issue of infusion pump devices can be air bubbles in the fluidic system, particularly in the pump system, but also in other components, such as the container. If air bubbles remain in the fluidic system, they may be administered instead of the liquid medicament leading to undesired dosing errors. Furthermore, the administration of air into a patient's body should be generally avoided for medical reasons.

One problem resulting from air in the fluidic system is the reduced stiffness of the fluidic system, due to the high compressibility of gases in relation to liquids such as water. This impedes detection of blockages or occlusions in the fluidic system by monitoring the fluidic pressure.

A syringe type-pump system for fluid dispensing arrays for multiwell plates is known. The syringe pump comprises a cylinder and a movable plunger, a first inlet conduit fluidly connected to a fluid reservoir, and a second outlet conduit connected toward a dispensing tip. A three-way port valve alternatingly connects the first conduit and the second conduit to the pump cylinder for refilling and for dispensing, respectively. The syringes are mounted vertically, in order to allow air bubbles in the pump cylinder to rise upward toward the exit port to the second conduit, so that they can be removed from the fluid system during the priming procedure, by conveying them through the second conduit and out of the dispensing tip. In order to prevent air bubbles that have been drawn into the pump cylinder volume during a first filling step of the priming procedure from accumulating in the dead volume between pump cylinder and valve and reentering again into the cylinder volume in the next filling step of the priming sequence, the dead volume is reduced to a minimum. For this the length of the conduit between the valve and the cylinder is minimized. Thus less air bubbles can accumulate in the dead volume. In some embodiments, special valves are used with a valve member that provides two different internal channels, one channel connecting the first conduit to the cylinder in the first state and the second channel connecting the second conduit to the cylinder. Thus air bubbles remaining in the second channel after the first priming cycle of drawing liquid into cylinder and expelling the liquid through the dispensing tip are not drawn again into the cylinder during the second priming cycle.

The priming of this syringe pump comprises at least two priming cycles of filling the pump cylinder and expunging the liquid through the outlet conduit. The priming of the disclosed pump functions only if the pump is in the intended orientation, since the correct path of air bubbles during the priming procedure is given by the direction of the buoyancy force in combination with the geometry of the pump elements.

When environmental atmospheric pressure changes, especially drops, within a short time, for example due to fast changes in height when travelling in elevators or mountainous areas, or due to cabin pressurization in air planes, air present in the dosing unit or the infusion tubing will expand. As a result an additional dose of liquid medicament is expelled from the fluid system into the body of the patient. A similar effect may occur in case of a change in temperature.

Since the health of a patient is of primary importance and needs to be protected, there is a need to improve the safety level of infusion pump devices by providing an improved dosing unit that has a dosing unit that minimizes dosing errors of various causes, minimizes the possible maximum dosing error, minimizes the amount of air in the fluidic system during filling, and allows a precise metering of liquid medicament that is reliable and producible with high quality at low costs in a large-scale manufacture.

SUMMARY

According to the present disclosure, a dosing unit for an ambulatory infusion pump device is presented. The dosing unit comprises a cylinder pump having a cylinder and a piston displaceable along a longitudinal axis of the cylinder. The piston has optically detectable markings allowing for the determination of an absolute position of the piston within the cylinder and/or of a relative displacement within the cylinder. The dosing unit further comprises a valve that can be in two operational states and a window on the cylinder for providing optical access to the optically detectable markings. The optical access window provides optical access to the optically detectable markings when the valve is in one of the two operational states and does not provide optical access to the optically detectable markings when the valve is between the two operational states Accordingly, it is a feature of the embodiments of the present disclosure to improve the safety level of infusion pump devices by providing an improved dosing unit that has a dosing unit that minimizes dosing errors of various causes, minimizes the possible maximum dosing error, minimizes the amount of air in the fluidic system during filling, and allows a precise metering of liquid medicament that is reliable and producible with high quality at low costs in a large-scale manufacture. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 8 illustrates a table with the contents of a FIFO register recording the amounts of administered liquid medicament and detected air for monitoring the air in the downstream fluidic system in a dosing method according to an embodiment of the present disclosure.

FIG. 9 illustrates another table with the contents of a FIFO register, for monitoring the air in the downstream fluidic system in another variant of a dosing method according to an embodiment of the present disclosure.

DETAILED DESCRIPTION

Figure 1:
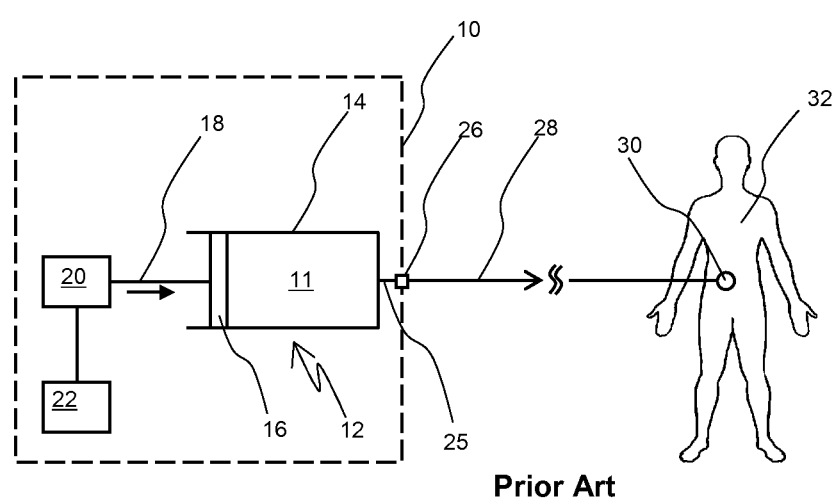
FIGS. 1a-b illustrate schematically a prior art infusion pump with a dosing unit of (a) the syringe drive type, and (b) the downstream pump type with primary reservoir and secondary pump cylinder reservoir.
Figure 1:
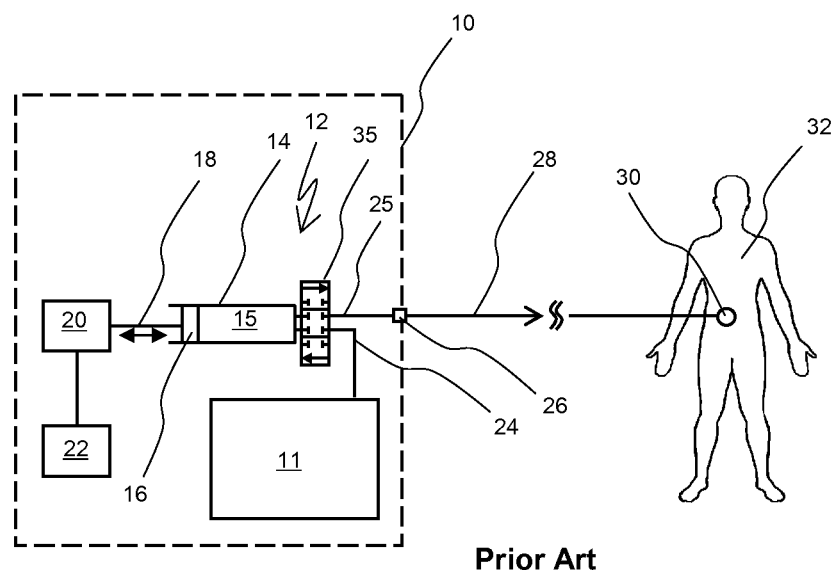

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A dosing unit for an ambulatory infusion pump device can have a cylinder pump comprising a cylinder and a piston slidably arranged in the cylinder. The piston can be operationally engaged with the cylinder and can be displaced along a longitudinal axis of the cylinder. The piston can comprise a scale that interacts with a sensor and provides a displacement signal indicative of a displacement of the piston in regard to the cylinder. Advantageously, the piston can have a shaft with a first threaded segment interacting with a threaded portion of the cylinder. The piston of the dosing unit can be displaced along a longitudinal axis of the cylinder by rotating the piston in regard to the cylinder around the axis.

In one embodiment, the piston can comprise markings that can be optically, magnetically or electrically detected.

In another embodiment, the piston shaft can comprise a second segment provided with optically detectable markings that allow the monitoring of the longitudinal and/or rotational displacement of the piston in regard to the cylinder.

In yet another embodiment, the optical markings can be at least two stripes arranged on the second shaft segment along the circumference of the shaft and parallel to the longitudinal axis. The optical markings can be optically distinguishable.

In one embodiment, the optical markings can be a plurality of circumferential rings arranged on the second shaft segment. The optical markings can be optically distinguishable. The second segment can be between the first threaded portion and the piston head or, alternatively, the second segment can at least partially overlap the first threaded portion.

In yet another embodiment, a window can be on the cylinder that can allow optical access to at least a part of the second segment of the piston shaft.

In yet another embodiment, the piston can modulate the frictional force between piston and cylinder during a movement of the piston.

An embodiment of the dosing unit can comprise a valve for alternatingly connecting the inner volume of the cylinder in a first state to an inlet conduit and in a second state to an outlet conduit. The valve can comprise a valve seat and a valve member. The valve member can be part of the cylinder. The cylinder can be rotatably or slidably mounted in a bearing of the valve seat such that the valve can be switched between the two states by rotating the cylinder with the valve member by a certain angle along longitudinal axis, or by displacing the cylinder with the valve member in regard to the valve seat by a certain distance along longitudinal axis.

In another embodiment, the dosing unit can comprise a valve that can be in two operational states and a window can be provided on the cylinder for providing access to the scale on the piston. The optical access window can provide access to the scale when the valve is in one of the two operational states and cannot provide access to the scale when the valve is between the two operational states.

A dosing unit for an ambulatory infusion pump device can have a cylinder pump comprising a cylinder and a piston displaceable along a longitudinal axis of the cylinder. The piston can have a piston head and a piston shaft. The piston shaft can have a segment with markings that can be optically, magnetically or electrically detected. The markings can a plurality of stripes on the second shaft segment along the circumference of the shaft and parallel to the longitudinal axis.

In one embodiment, the marker segment of the shaft can have markings in the form of at least two stripes on the marker segment along the circumference of the shaft and parallel to the longitudinal axis.

In another embodiment, the marker segment of the shaft can have markings in the form of a plurality of circumferential rings on the second shaft segment along the longitudinal axis.

Advantageously in some dosing units, the markings can be optically detectable stripes.

A dosing unit can comprise a valve that can be in two operational states and a window provided on the cylinder for providing optical access to the optically detectable stripes. The optical access window can provide optical access to the optically detectable stripes when the valve is in one of the two operational states and cannot provide optical access to the optically detectable stripes when the valve is between the two operational states.

In some embodiments, the piston shaft can comprise a threaded segment interacting with a threaded portion of the cylinder in such a way that the piston can be displaced along the longitudinal axis when the piston shaft is rotated around the axis.

Such a dosing unit can offer the possibility to precisely determine the linear displacement of the piston without the need of high precision sensor elements or markings. The relation between rotation angle and linear displacement can be given by the construction of the dosing unit and thus can be precisely known. Since a comparably large rotation angle of the piston can correspond to a comparably small linear displacement, or dosing volume respectively, a comparably coarse distribution of the markings along the circumference of the shaft can correspond to a fine detection grid along the linear axis.

Advantageously, the second marker segment of the dosing unit can be between the first threaded segment and the piston head.

Additionally or alternatively, the second marker segment can at least partially overlap the first threaded segment.

The dosing unit can have a valve for alternatingly connecting the inner volume of the cylinder in a first state to an inlet conduit and in a second state to an outlet conduit. The valve can comprise a valve seat and a valve member. The valve member can be part of the cylinder. The cylinder can be rotatably or slidably mounted in a bearing of the valve seat such that the valve can be switched between the two states by rotating the cylinder with the valve member by a certain angle along the longitudinal axis of the cylinder, or by displacing the cylinder with the valve member in regard to the valve seat by a certain distance along the longitudinal axis.

Another dosing unit for an ambulatory infusion pump device can have a cylinder pump comprising a cylinder and a piston displaceable along a longitudinal axis of the cylinder. The piston can have optically detectable markings that can allow the determination of an absolute position of the piston within the cylinder and/or of a relative displacement within the cylinder. The dosing unit can comprise a valve that can be in two operational states and a window can be provided on the cylinder for providing optical access to the optically detectable markings. The optical access window can provide optical access to the optically detectable markings when the valve is in one of the two operational states and cannot provide optical access to the optically detectable markings when the valve is between the two operational states.

Such a dosing unit can offer, for example, the advantage that the piston displacement detection can be switched off in an easy and failure proof way as long as the valve is not operational. Another advantage can be the indirect check of the correct valve position. If the pump is activated and no piston displacement is detected, this can be the result of the valve not being in an operational state. In such a case, the administration process can be interrupted and a failure message can be issued by a control system.

In one embodiment, the piston shaft of the piston can have a marker segment, on which the optical markings can be in the form of at least two stripes on the second shaft segment along the circumference of the shaft and parallel to the longitudinal axis.

In an alternative embodiment, the piston shaft of the piston can have a marker segment on which the optical markings can be provided in a plurality of optically distinguishable circumferential rings on the second shaft segment.

In an embodiment, the piston can comprise a piston head and a piston shaft with a threaded segment interacting with a threaded portion of the cylinder in such a way that the piston can be displaced along the longitudinal axis when the piston shaft is rotated around the axis.

The second marker segment of the dosing unit can be between the first threaded segment and the piston head.

Additionally or alternatively, the second marker segment can at least partially overlap the first threaded segment.

A dosing unit can comprise a valve for alternatingly connecting the inner volume of the cylinder in a first state to an inlet conduit and in a second state to an outlet conduit. The valve can comprise a valve seat and a valve member. The valve member can be part of the cylinder. The cylinder can be rotatably or slidably mounted in a bearing of the valve seat such that the valve can be switched between the two states by rotating the cylinder with the valve member by a certain angle along the longitudinal axis of the cylinder, or by displacing the cylinder with the valve member in regard to the valve seat by a certain distance along the longitudinal axis.

An infusion pump device can comprise a dosing unit as discussed or can be designed to receive such a dosing unit.

An embodiment of the infusion pump device can comprise one or more sensor units that can detect the markings of the piston of the dosing unit mounted in the infusion pump device and an evaluation unit that based on the signal received from the one or more sensor units can determine an absolute position of the piston within the cylinder of the dosing unit and/or of a relative displacement of the piston within the cylinder.

In one embodiment, the markings of the piston of the dosing unit mounted in the infusion pump device can be optical markings. The dosing unit can comprise a valve that can be in two operational states and a window can be provided on the cylinder that can allow optical access to the optical markings of the piston. The optical access window and the one or more sensor units of the infusion pump device can be arranged in such a way that the one or more sensor units can have optical access to the optical markings when the valve is in one of the two operational states and can have no optical access to the optical markings when the valve is between the two operational states.

A further embodiment can comprise a sensor that can detect a scale of a piston of a dosing unit mounted in the infusion pump device, thereby obtaining a displacement signal that can be indicative for a displacement of the piston in regard to a cylinder of the dosing unit.

Another embodiment can comprise an optical sensor for detecting markings on a piston shaft of the piston of the dosing unit.

A kit can comprise an infusion pump and one or more dosing units.

Another embodiment of an infusion pump device can have a primary reservoir for liquid medicament, a pump with a secondary reservoir that can be able to retrieve liquid medicament from the primary reservoir and to subsequently dosing the liquid medicament from the secondary reservoir in incremental steps, a first upstream conduit fluidly connecting the primary reservoir with the pump, a second downstream conduit fluidly connected to the pump for transporting the liquid medicament to an infusion site interface, a valve for alternatingly connecting the pump to one of the two conduits, and a control unit to control the operation of the infusion pump device. For filling the fluidic system of the infusion pump device with liquid medicament prior to infusion operation, the control unit can cause the infusion pump device to carry out the following steps: (a) bringing the pump to an initial state where an inner volume of the secondary reservoir is minimal; (b) switching the valve to a first state, in which the secondary reservoir is connected to the first conduit and the primary reservoir; (c) retrieving liquid medicament from the primary reservoir, wherein the retrieved liquid volume $V_C$ is at least equal to the inner volume $V_B$ of the first upstream conduit; (d) switching the valve to a second state, in which the secondary reservoir is connected to the second downstream conduit; (e) expelling the contents in the secondary reservoir into the second downstream conduit; (f) switching the valve to the first state; (g) retrieving liquid medicament from the primary reservoir, wherein the retrieved liquid volume $V_C$ is at least equal to the inner volume $V_D+V_E+V_F$ of the second downstream conduit; (h) switching the valve to the second state; and (i) expelling the contents in the secondary reservoir into the second downstream conduit by shifting the piston to the initial position.

One embodiment of the infusion pump device can have a primary reservoir for liquid medicament, a pump with a secondary reservoir that can retrieve liquid medicament from the primary reservoir and subsequently dose the liquid medicament from the secondary reservoir in incremental steps, a first upstream conduit fluidly connecting the primary reservoir with the pump, a second downstream conduit fluidly connected to the pump for transporting the liquid medicament to an infusion site interface, a valve for alternatingly connecting the pump to one of the two conduits, and a control unit to control the operation of the infusion pump device. For filling the fluidic system of the infusion pump device with liquid medicament prior to infusion operation, the control unit can cause the infusion pump device to carry out the following steps: (a) bringing the pump to an initial state where an inner volume of the secondary reservoir is minimal; (b) switching the valve to a first state, in which the secondary reservoir is connected to the first conduit and the primary reservoir, and retrieving a volume of liquid medicament from the primary reservoir; (c) switching the valve to a second state, in which the secondary reservoir is connected to the second downstream conduit, and expelling the contents in the secondary reservoir into the second downstream conduit; and (d) switching the valve to the first state, and retrieving a volume of liquid medicament from the primary reservoir; and (e) switching the valve to the second state; and expelling the contents in the secondary reservoir into the second downstream conduit. The retrieved liquid volume $V_{up}$ in step (b) can be at least equal the inner volume $V_B$ of the first upstream conduit, $V_{up} \geq V_B$; and the retrieved liquid volume $V_{Down}$ in step (d) is at least equal the inner volume $(V_D+V_E+V_F)$ of the second downstream conduit, $V_{Down} \geq (V_D+V_E+V_F)$.

The retrieved liquid volume $V_{up}$ in step (b) can be $V_{Up}=V_B*SF_{Up}$, with $SF_{Up}$ being a factor with $1.0 \leq SF_{Up} \leq 2.0$; and/or the retrieved liquid volume $V_{Down}$ in step (d) can be $V_{Down}=(V_D+V_E+V_F)*SF_{Down}$, with $SF_{Down}$ being a factor with $1.0 \leq SF_{Up} \leq 2.0$. The factor $SF_{Up}$, and/or the factor $SF_{Down}$ can be less or equal 1.5.

The resulting reduction of the volume of liquid that is needed for priming the upstream fluid system and the downstream fluid system can offer the advantage that the amount of liquid that can be used for priming and as a result cannot be administered, can be minimal. This can be particularly important for highly potent and expensive liquid medicaments, such as for example insulin, for infusion pumps having only a small available reservoir volume, such as for example ambulatory infusion pumps, and for infusion pumps that regularly need re-priming, for example after exchanging a primary reservoir, a disposable pump part or an infusion line.

In such an infusion pump device, prior to retrieving liquid medicament from the primary reservoir, the control unit can verify that the remaining content of the primary reservoir can be sufficient for the next step of the filling procedure, or for all following steps of the filling procedure. It can be advantageous in such an embodiment, if in case the control unit finds the remaining content of the primary reservoir to be not sufficient, the control unit can request a user to replace or refill the primary reservoir.

During the filling procedure, the control unit can monitor the pressure in the second downstream conduit. This can allow detecting occlusions in the downstream conduit.

The infusion pump device can also comprise a detector that can detect the presence of air bubbles in the second downstream conduit.

The pump can be a cylinder pump with a cylinder as the secondary reservoir and a piston that can be slidably arranged within the cylinder.

In a further embodiment of the infusion pump device, during the filling procedure, the control unit can monitor the accumulated amount of air in the second downstream conduit. In such an embodiment, it can be advantageous when control unit repeats the filling procedure when the accumulated amount of air exceeds a certain threshold value.

In a method for priming an infusion pump device with a primary reservoir for liquid medicament, a pump with a secondary reservoir that can retrieve liquid medicament from the primary reservoir and can subsequently dose the liquid medicament from the secondary reservoir in incremental steps, a first upstream conduit fluidly connecting the primary reservoir with the pump, a second downstream conduit fluidly connected to the pump for transporting the liquid medicament to an infusion site interface, and a valve for alternatingly connecting the pump to one of the two conduits, the followings steps can be carried out for filling the fluidic system of the infusion pump device with liquid medicament prior to infusion operation: (a) bringing the pump to an initial state where an inner volume of the secondary reservoir is minimal; (b) switching the valve to a first state, in which the secondary reservoir is connected to the first conduit and the primary reservoir; (c) retrieving liquid medicament from the primary reservoir, wherein the retrieved liquid volume $V_C$ is at least equal to the inner volume $V_B$ of the first upstream conduit; (d) switching the valve to a second state, in which the secondary reservoir is connected to the second downstream conduit; (e) expelling the contents in the secondary reservoir into the second downstream conduit; (f) switching the valve to the first state; (g) retrieving liquid medicament from the primary reservoir, wherein the retrieved liquid volume $V_C$ is at least equal to the inner volume $V_D+V_E+V_F$ of the second downstream conduit; (h) switching the valve to the second state; and (i) expelling the contents in the secondary reservoir into the second downstream conduit by shifting the piston to the initial position.

In one embodiment of the method, a pump with a secondary reservoir that can retrieve liquid medicament from the primary reservoir and can subsequently dose the liquid medicament from the secondary reservoir in incremental steps, a first upstream conduit fluidly connecting the primary reservoir with the pump, a second downstream conduit fluidly connected to the pump for transporting the liquid medicament to an infusion site interface, a valve for alternatingly connecting the pump to one of the two conduits, and a control unit configured to control the operation of the infusion pump device, the followings steps are carried out for filling the fluidic system of the infusion pump device with liquid medicament prior to infusion operation: (a) bringing the pump to an initial state where an inner volume of the secondary reservoir is minimal; (b) switching the valve to a first state, in which the secondary reservoir is connected to the first conduit and the primary reservoir, and retrieving a volume of liquid medicament from the primary reservoir; (c) switching the valve to a second state, in which the secondary reservoir is connected to the second downstream conduit, and expelling the contents in the secondary reservoir into the second downstream conduit; (d) switching the valve to the first state, and retrieving a volume of liquid medicament from the primary reservoir; and (e) switching the valve to the second state; and expelling the contents in the secondary reservoir into the second downstream conduit. The retrieved liquid volume $V_{up}$, in step (b) is at least equal the inner volume $V_B$ of the first upstream conduit, $V_{up} \geq V_B$; and the retrieved liquid volume $V_{Down}$ in step (d) is at least equal the inner volume $(V_D+V_E+V_F)$ of the second downstream conduit, $V_{Down} \geq (V_D+V_E+V_F)$.

The retrieved liquid volume $V_{up}$ in step (b) can be $V_{Up}=V_B*SF_{Up}$, with $SF_{Up}$ being a factor with $1.0 \leq SF_{Up} \leq 2.0$; and/or the retrieved liquid volume $V_{Down}$ in step (d) can be $V_{Down}=(V_D+V_E+V_F)*SF_{Down}$, with $SF_{Down}$ being a factor with $1.0 \leq SF_{Up} \leq 2.0$. The factor $SF_{Up}$, and/or the factor $SF_{Down}$ can be less or equal 1.5.

In one embodiment, prior to retrieving liquid medicament from the primary reservoir, it can be verified that the remaining content of the primary reservoir can be sufficient for the next step of the filling procedure, or for all following steps of the filling procedure. If the remaining content of the primary reservoir is found to be not sufficient, the primary reservoir can be replaced or refilled before the filling procedure can be carried out.

In another embodiment, during the filling procedure, the pressure in the second downstream conduit can be monitored. This can allow detecting occlusions in the downstream conduit.

In a further embodiment, during the filling procedure, the presence of air bubbles in the second downstream conduit can be detected.

In yet another embodiment, the pump can be a cylinder pump with a cylinder as the secondary reservoir and a piston can be slidably arranged within the cylinder.

During the filling procedure, the accumulated amount of air in the second downstream conduit can be monitored. In one embodiment, the filling procedure can be repeated when the accumulated amount of air exceeds a certain threshold value. Such a priming method can be carried out with an infusion pump device.

Another infusion pump device can comprise a primary reservoir for the liquid medicament, a pump with a secondary reservoir that can retrieve liquid medicament from the primary reservoir and can subsequently dose the liquid medicament from the secondary reservoir in one or more portions of adjustable volume $V_{dose,i}$ to a downstream conduit, and a control unit can control the operation of the infusion pump device. For metering the multitude of portions $V_{dose,i}$, the control unit can cause the infusion pump device to carry out the following steps: (a) determining a maximum refill level $V_{C,max}$ for the secondary reservoir, based on given external parameters, wherein the maximum refill level does not exceed the maximum capacity of the secondary reservoir; (b) filling the secondary reservoir with liquid medicament from the primary reservoir to the maximum refill level $V_{C,max}$; (c) metering and conveying the multitude of portions of liquid medicament to the downstream conduit; (d) if the secondary reservoir becomes empty, refilling the secondary reservoir as in step (b) and continuing with step (c).

A further infusion pump device can comprise a primary reservoir for liquid medicament, a pump with a secondary reservoir that can retrieve liquid medicament from the primary reservoir and can subsequently dose the liquid medicament from the secondary reservoir in one or more portions of adjustable volume $V_{dose,i}$ to a downstream conduit, and a control unit can control the operation of the infusion pump device. For metering the multitude of portions $V_{dose,i}$ the control unit can cause the infusion pump device to carry out the following steps: (a) filling the secondary reservoir with liquid medicament from the primary reservoir to a certain adjustable refill level $V_{refill}$; (b) metering and conveying at certain points in time $t_i$ the different portions $V_{dose,i}$ of liquid medicament to the downstream conduit; and (c) if the secondary reservoir becomes empty, refilling the secondary reservoir as in step (a) and continuing with step (b). The control unit on a regular basis can determine a maximum refill level $V_{C,max}$ for the secondary reservoir or can retrieve such a maximum refill level $V_{C,max}$ from another source, e.g. a memory unit, wherein the volumes $V_{dose,i}$ of the one more portions of liquid medicament to be metered and the points in time $t_i$ at which they can be metered and conveyed are independent from the maximum refill level $V_{C,max}$. During the metering of the multitude of portions $V_{dose,i}$ the control unit can restrict the filling of the secondary reservoir in step (a) to a refill level $V_{refill}$ that can be smaller or equal the maximum refill level $V_{C,max}$.

Such an embodiment of an infusion pump device can provide the possibility to restrict the volume of liquid that can be present in the secondary reservoir at any time to a certain value, thereby generally reducing the risk related to any major malfunction, without having an influence on the normal operation of the device, namely the administration of the distinct doses of liquid medicament.

In one embodiment of the infusion pump device, if the secondary reservoir becomes empty during the metering of a single portion of liquid medicament and has to be refilled, the maximum refill level for that particular refilling step can be increased to an increased maximum refill level $V_{C,max}'=V_{C,max}+V_{dose,rem}$, with $V_{dose,rem}$ being the remaining volume of the single portion that has not yet been completely metered.

In another embodiment of the infusion pump device, if the next single portion $V_{dose,i}$ of liquid medicament to metered is above a certain threshold, the secondary reservoir can be refilled to the maximum refill level prior or after administration of the single portion.

In a further embodiment of the infusion pump device, if the secondary reservoir becomes empty during the metering of the next single portion ($V_{dose,i,next}$) of liquid medicament, prior to metering the next portion, the secondary reservoir can be refilled with liquid medicament from the primary reservoir, to an increased maximum refill level $V_{C,max}'= V_{C,max}+V_{dose,i,next}$, with $V_{dose,i,next}$ being the volume of the single portion that is to be metered next.

In yet another embodiment of the infusion pump device, if the secondary reservoir becomes empty during the metering of a single portion of liquid medicament and has to be refilled, the refilling of the secondary reservoir can be divided in two steps. In a first step, the secondary reservoir can be filled with liquid medicament from the primary reservoir to a volume level $V_{dose,rem}$, with $V_{dose,rem}$ being the remaining volume of the single portion that has not yet been completely metered, and the remaining volume can be metered and conveyed. In a second step, the secondary reservoir can be filled to the maximum refill level $V_{C,max}$.

In such infusion pump devices, the maximum refill level $V_{C,max}$ of the secondary reservoir can be proportional to the amount of liquid to be expected to be metered within a certain time period.

It can be advantageous if in such infusion pump devices the control unit or a separate system on a regular basis can recalculate the maximum refill level $V_{C,max}$ as a function of the average volume of liquid that has been metered within a certain time period in the past, and if the recalculation has been carried out by a separate system can subsequently provide the recalculated maximum refill level $V_{C,max}$ to the control unit, e.g., by storing it in a memory unit. In one embodiment, the maximum refill level $V_{C,max}$ can be recalculated based on the average volume of liquid that has been metered within a period that can include at least the last 24 hours. In another embodiment, the period can include at least the last 48 hours, or even a week. This can have the advantage that $V_{C,max}$ can adjust to changes in the average total daily dose, which may change over time, due to changing physical conditions of a patient.

In another embodiment, the maximum refill level $V_{C,max}$ of the secondary reservoir can be adjusted when one or more of the given external parameters change.

In yet another embodiment, one or more sensor units can be provided that can change in environmental temperature and/or environmental pressure.

In a further embodiment, the control unit or a separate system on a regular basis can recalculate the maximum refill level $V_{C,max}$ as a function of the changes in environmental temperature and/or environmental pressure within a certain time period in the past, and if the recalculation has been carried out by a separate system can subsequently provide the recalculated maximum refill level $V_{C,max}$ to the control unit, e.g., by storing it in a memory unit.

In a method for operating an infusion pump device that can comprise a primary reservoir for the liquid medicament and a pump with a secondary reservoir that can retrieve liquid medicament from the primary reservoir and can subsequently deliver the liquid medicament from the secondary reservoir in one or more portions of adjustable volume $V_{dose,i}$ to a downstream conduit, the followings steps can be carried out for metering the multitude of portions $V_{dose,i}$: (a) determining a maximum refill level $V_{C,max}$ for the secondary reservoir, based on given external parameters, wherein the maximum refill level does not exceed the maximum capacity of the secondary reservoir; (b) filling the secondary reservoir with liquid medicament from the primary reservoir to the maximum refill level $V_{C,max}$; (c) metering and conveying the multitude of portions of liquid medicament to the downstream conduit; (d) if the secondary reservoir becomes empty, refilling the secondary reservoir as in step (b) and continuing with step (c).

In another method for operating an infusion pump device can comprise a primary reservoir for the liquid medicament, and a pump with a secondary reservoir that can retrieve liquid medicament from the primary reservoir and can subsequently convey the liquid medicament from the secondary reservoir in one or more portions of adjustable volume $V_{dose,i}$ to a downstream conduit, for metering the multitude of portions $V_{dose,i}$ the following steps can be carried out: (a) filling the secondary reservoir with liquid medicament from the primary reservoir to a certain adjustable refill level $V_{refill}$; (b) metering and conveying at certain points in time $t_i$ the different portions $V_{dose,i}$ of liquid medicament to the downstream conduit; and (c) if the secondary reservoir becomes empty, refilling the secondary reservoir as in step (a) and continuing with step (b). On a regular basis a maximum refill level $V_{C,max}$ for the secondary reservoir can be determined, or can be retrieved from another source, e.g. a memory unit, wherein the volumes $V_{dose,i}$ of the one more portions of liquid medicament to be metered and the points in time $t_i$ at which they can be metered and conveyed are independent from the maximum refill level $V_{C,max}$. During the metering of the multitude of portions $V_{dose,i}$ the filling of the secondary reservoir in step (a) can be restricted to a refill level $V_{refill}$ that can be smaller or equal the maximum refill level $V_{C,max}$.

Such an embodiment can allow restriction of the volume of liquid that can be present in the secondary reservoir at any time to a certain value, thereby generally reducing the risk related to any major malfunction, without having an influence on the normal operation of the device, namely the administration of the distinct doses of liquid medicament.

In one embodiment, if the secondary reservoir becomes empty during the metering of a single portion of liquid medicament and has to be refilled, the maximum refill level for that particular refilling step can be increased to an increased maximum refill level $V_{C,max}'=V_{C,max}+V_{dose,rem}$, with $V_{dose,rem}$ being the remaining volume of the single portion that has not yet been completely metered.

In another embodiment, if the next single portion $V_{dose,i}$ of liquid medicament to metered is above a certain threshold, the secondary reservoir can be refilled to the maximum refill level prior or after administration of the single portion.

In a further embodiment, if the secondary reservoir becomes empty during the metering of the next single portion ($V_{dose,i,next}$) of liquid medicament, prior to metering the next portion, the secondary reservoir can be refilled with liquid medicament from the primary reservoir, to an increased maximum refill level $V_{C,max}'=V_{C,max} V_{dose,i,next}$, with $V_{dose,i,next}$ being the volume of the single portion that can be metered next.

In yet another embodiment, if the secondary reservoir becomes empty during the metering of a single portion of liquid medicament and has to be refilled, the refilling of the secondary reservoir can be divided in two steps. In a first step, the secondary reservoir can be filled with liquid medicament from the primary reservoir to a volume level $V_{dose,rem}$, with $V_{dose,rem}$ being the remaining volume of the single portion that has not yet been completely metered, and the remaining volume can be metered and conveyed. In a second step, the secondary reservoir can be filled to the maximum refill level $V_{C,max}$.

In such methods, the maximum refill level $V_{C,max}$ of the secondary reservoir can be proportional to the amount of liquid expected to be metered within a certain time period. Furthermore, it can be advantageous to recalculate on a regular basis the maximum refill level $V_{C,max}$ as a function of the average volume of liquid that has been metered within a certain time period in the past. In one embodiment, the maximum refill level $V_{C,max}$ can be recalculated based on the average volume of liquid that has been metered within a period that includes at least the last 24 hours. In another embodiment, the period can include at least the last 48 hours, or even a week. This can have the advantage that $V_{C,max}$ can adjust to changes in the average total daily dose, which may change over time, due to changing physical conditions of a patient.

It can also be advantageous for such methods when the maximum refill level $V_{C,max}$ of the secondary reservoir can be adjusted when one or more of the given external parameters change.

In a further embodiment, one or more sensor units can be provided that can detect changes in environmental temperature and/or environmental pressure.

In yet another embodiment, the maximum refill level $V_{C,max}$ can be recalculated on a regular basis as a function of the changes in environmental temperature and/or environmental pressure within a certain time period in the past. Such a method can be carried out with an infusion pump device.

To achieve low dosing errors during the administration of liquid medicament, precise metering of the liquid medicament can be important. In a dosing unit that can allow metering from the secondary interval in small incremental doses by dividing the full piston stroke into a larger number of partial strokes piston pump acting as a secondary reservoir, this can require exact knowledge of the piston position within the cylinder at any time.

In the prior art syringe-type infusion pump device, the displacement of the piston within the primary reservoir cartridge can be determined only indirectly. The drive unit motor can be provided with a sensor that can detect the rotation of the motor axis. Based on the number of rotations and the known thread pitch of the threaded piston shaft, the displacement of the piston in the primary reservoir cartridge can be determined. However, if the operational coupling between motor and piston shaft is not functional for some reason, e.g., due to a damaged thread or gear, the pump device can determine a displacement of the piston although the piston may not be moving at all. The result of such a failure may be an undetectable dosing error. This can be particularly relevant for syringe-type piston pumps because the drive unit motor can only be temporarily coupled to the piston of the disposable cartridge and every replacement of the cartridge can bear the risk of a technical failure. Additionally, the large diameter of the cartridge and the elasticity of the drive train may result in the motor rotation not being translated into a correct plunger displacement.

In a dosing unit for an infusion pump device, an exact and failsafe metering can be achieved by directly detecting the movement of the piston shaft of the cylinder pump. In the case, for example, of a threaded piston shaft rotating during displacement, the relative displacement can be determined based on the determined number of evolutions and the thread pitch. It can be also possible to determine the absolute position of the piston, by initializing the zero position, where the piston head can touch the end of the cylinder.

Figure 5:
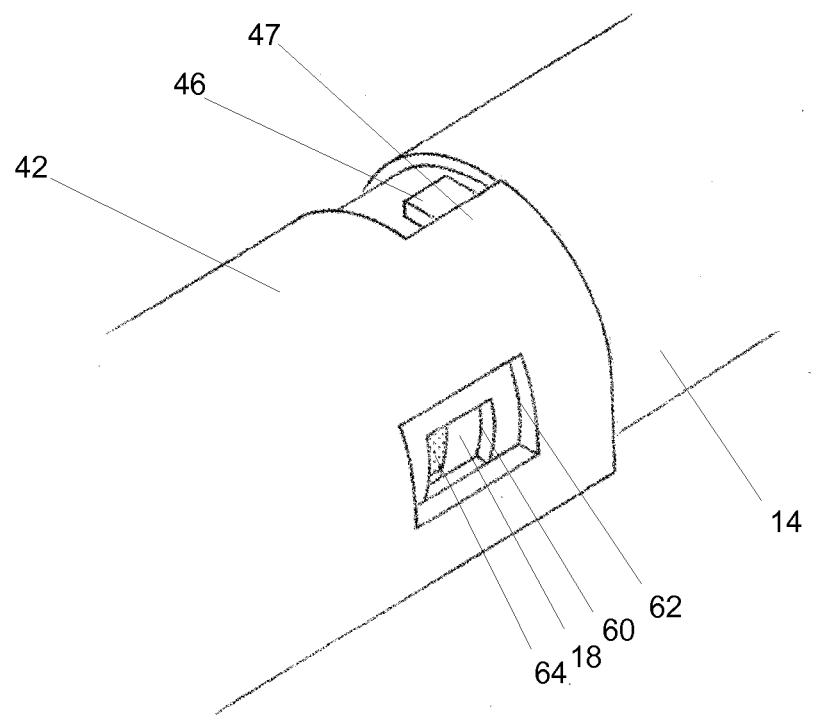
FIG. 5 illustrates schematically shows a detail the dosing unit of FIG. 3 in the area of the detection windows according to an embodiment of the present disclosure.
Figure 3:
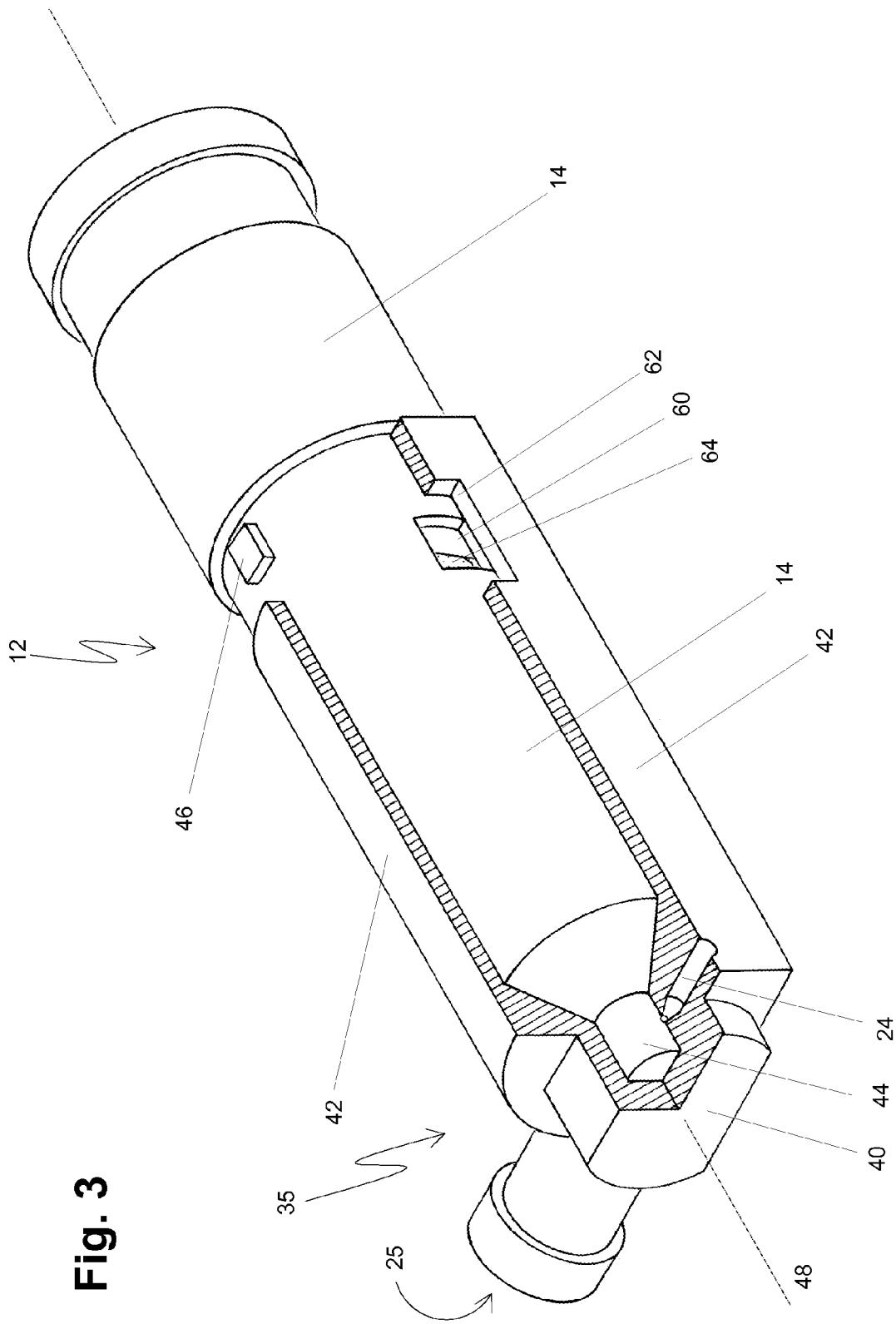
FIG. 3 illustrates schematically a dosing unit with a partial sectional view of the valve seat and view on the pump cylinder and valve member according to an embodiment of the present disclosure.
Figure 4:
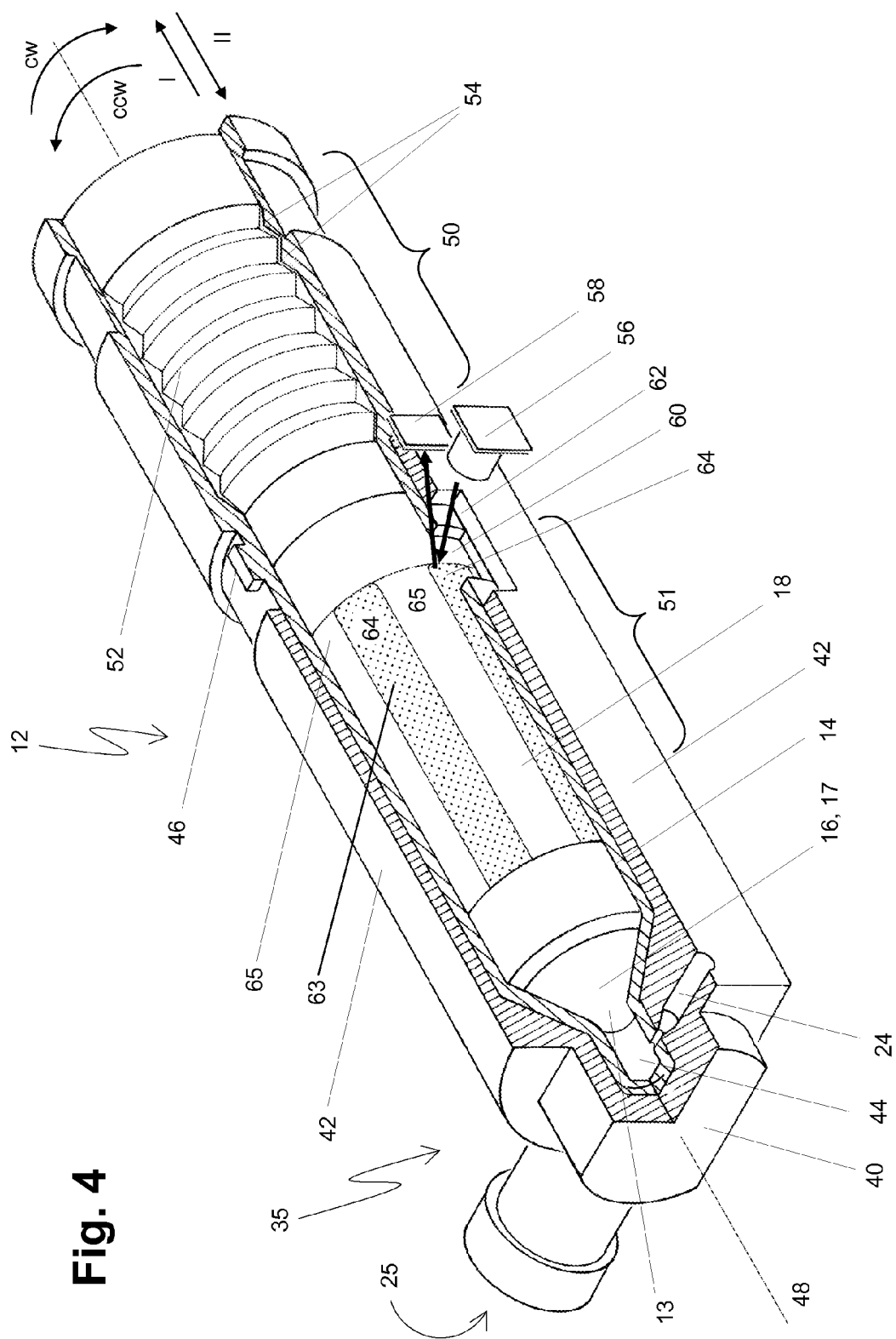
FIG. 4 illustrates schematically the dosing unit of FIG. 3 in a partial sectional view of the cylinder and view on the pump piston according to an embodiment of the present disclosure.

One possible embodiment of a dosing unit is depicted in FIGS. 3 to 5, schematically showing a partial sectional view on the dosing unit 12, comprising a cylinder pump, the cylinder pump comprising a cylinder 14, a piston 16 and a valve 35. The front end of cylinder 14 can act as a rotatable valve member 44, interacting with the valve seat 40. The valve can switch between a first state, where an inlet conduit 24 can be fluidly connected to the inner volume 13 of the pump cylinder, and a second state, where an outlet conduit 25 can be fluidly connected to the inner volume 13. In FIGS. 3 to 5, the valve can be in the second position, where the pump can expel the liquid medicament in the pump cylinder into the downstream fluidic system and towards the patient. Downstream of the shown outlet conduit 25, an air sensor and an occlusion sensor can be arranged in the dosing unit.

The cylinder 14 can be rotatably arranged in bearing 42 of the valve 35. By rotating the cylinder along its longitudinal axis 48 by a certain angle, the valve can be switched between the first and the second state. A cam 46 on the cylinder can interact with two stoppers (of which only one 47 is visible in the Fig.) on the valve bearing 42, thereby defining the two discrete valve positions.

The piston shaft 18, which can be connected to a drive motor (not shown), can comprise a first segment 51, directly behind the piston head 17, and a second, threaded segment 50. The outer thread 52 of the shaft can interact with a short inner thread segment 54 on the cylinder. A rotation of the piston 16 along axis 48 in counter clockwise (ccw) direction can lead to a linear displacement in direction I, increasing the inner volume, while a clockwise rotation (cw) can lead to a linear displacement in direction II, decreasing the inner volume.

The static and dynamic friction between piston thread 52 and cylinder thread 54, the static and dynamic friction between piston head 17 and the wall of cylinder 14, and the static and dynamic friction between the cylinder bearing and the cylinder can be chosen such that a coupled motion between the rotating piston 16, driven by a drive unit (not shown), and the cylinder 14 can occur as long as the motion of the cylinder in the bearing cannot be blocked. This can be the case when the static (and thus also the dynamic) friction between cylinder and bearing can be smaller than the sum of the static friction between cylinder and piston head and between piston thread and cylinder thread.

When the cam 46 abuts one of the two stoppers 47, and thus the motion of the cylinder in the bearing can be blocked, this can be equivalent to a very high static friction between cylinder bearing and cylinder. The static friction between cylinder and bearing can be now larger than the sum of the static friction between piston head and cylinder and piston thread and cylinder thread. Cylinder and piston can be now decoupled, and the rotating piston 18 can start to displace within the now static cylinder 14.

In FIG. 3, the piston head 17 has reached the end of the cylinder 14, where the inner volume 13 of the cylinder can be minimal. A further displacement of the piston may not be possible, which can be registered by the driving unit. The absolute position of the piston 16 can be now clearly defined and can be reset in the controller unit to zero. When now the rotation of the piston can be reversed to counter-clockwise, no stopper can be in the path of the cam 46, and the cylinder and the piston can be motionally coupled again, resulting in a rotation of the cylinder in the bearing until cam 46 can reach the other stopper (not visible). The valve has been switched to the first state, and the piston can be decoupled again from the cylinder. The piston can move now in direction I and can suck liquid medicament into the cylinder from the primary reservoir through inlet conduit 24. After having retrieved the necessary amount of liquid, the rotation of the piston can be reversed again to clockwise and the valve can be switched to the second state. The dosing unit can now be ready to convey liquid in the required doses.

In a dosing unit, the real displacement of the piston can be determined by directly detecting the rotation of the piston shaft. For that purpose, the first segment 51 of the shaft can be provided with markings that can be optically distinguished. For example, such markings can be as longitudinal black 64 and white 65 markings, as shown in FIG. 3. This may, however, not be essential. They may also be white or grey, or of different colors, or provided with different reflection values, and the like.

The cylinder wall 14 and the valve bearing 42 can have overlapping windows 60, 62, realized as holes (as shown in the Figures) or transparent portions. These overlapping windows 60, 62 can allow optical access to the markings. A light emitting element 56, for example an LED, can illuminate the markings and a photo sensor 58 can detect the light reflected by the markings, which, for example, can have low amplitude for black markings and high amplitude for white markings. The rotation of the piston shaft can thus be determined by counting the changes between the markings, respectively by counting the rising and falling edges in the corresponding oscillating signal delivered by the photosensor 58.

The piston shaft 18 can have four black markings 64 and four white markings 65. This can result in a detectable signal (rising or falling edge) every 45° of the rotation, which together with a quite flat thread pitch can allow a very precise displacement of the piston in the longitudinal direction, and thus a very precise metering precision.

A property of such a dosing device with a rotary encoder being integral with or rigidly attached to the piston shaft can be the fact that the measured signal can be directly connected to the actual rotation of the piston. If the coupling between motor and piston is impaired, this event can be immediately recognized, without the risk of a potentially hazardous dosing error. Any technical failure in the drive train, such as a faulty coupling between piston and drive unit, or a broken transmission shaft, or the like, which with a state of the art device may go unnoticed, can be detected.

The dosing volume may be controlled by either activating the pump drive during a certain time or by activating the drive unit until a certain displacement has been achieved. In the first approach, the piston displacement information can be used to check if accuracy remains within a certain limit and to readjust the drive unit if necessary. In the latter approach, the necessary resolution of the displacement encoding can be higher.

The markings 64, 65 may of course be chosen in other colors, depending on the sensor and illumination system. The markings can be produced for example by suitable coating or printing techniques, or by two component injection molding.

In an alternative embodiment, the markings may be provided as circumferential rings instead of longitudinal stripes. With such a linear encoder, the detected light signal can directly correlate to the longitudinal displacement of the piston.

In the embodiment given in FIGS. 3, 4, 5, two overlapping windows can be provided. While this embodiment can have additional advantages that will be discussed further below, for the basic principle, it can be sufficient to provide a window 60 only in the wall of the cylinder 14, if the bearing 42 can be constructed in a way that it cannot cover the window 60.

Figure 6:
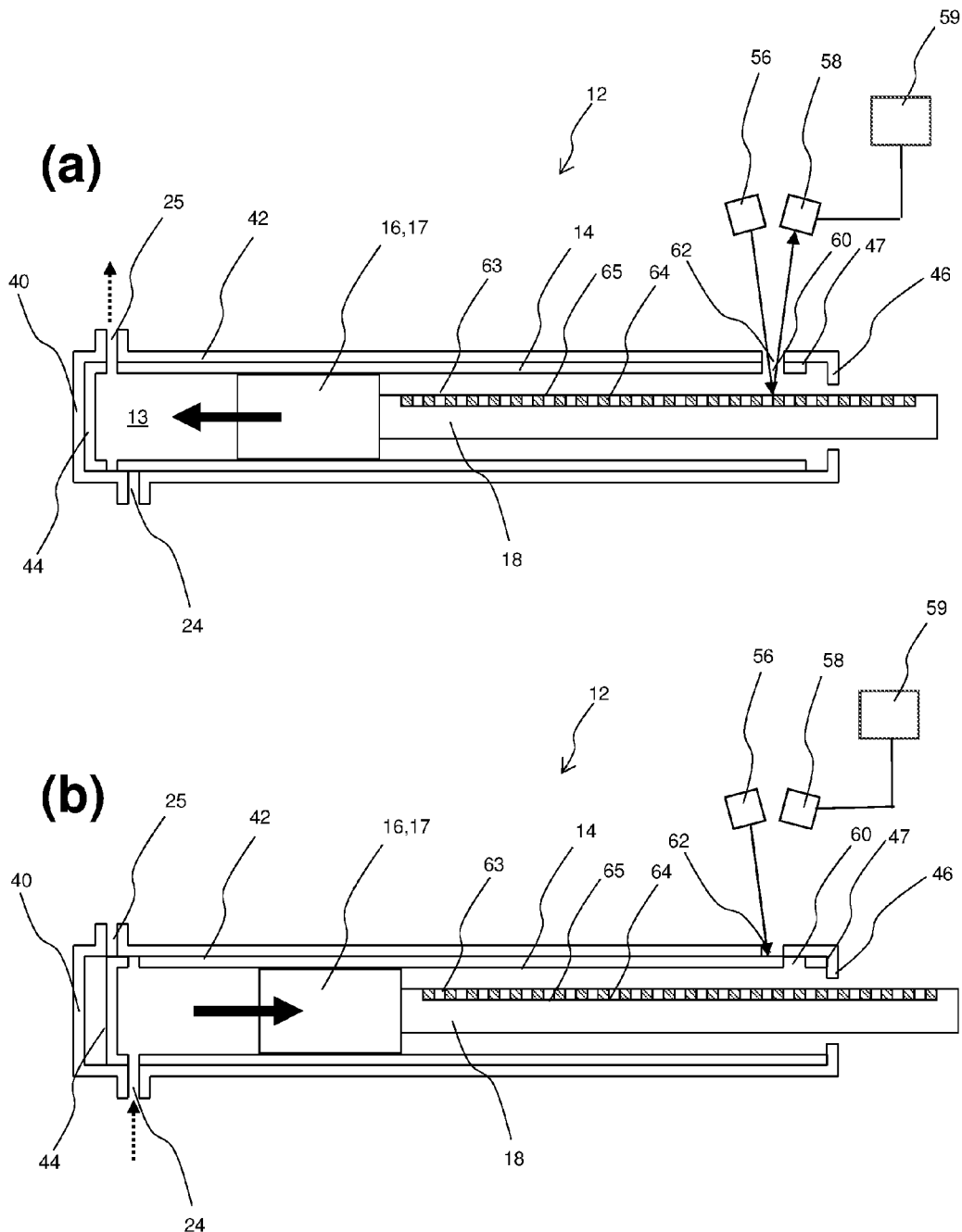
FIG. 6a-b illustrate schematically a cross-section of a dosing unit according to the invention, (a) when expelling the liquid from the cylinder and (b) when retrieving new liquid according to another embodiment of the present disclosure.

FIG. 6 schematically shows a cross-section of another embodiment of a dosing unit with a piston 16 that can be slidingly displaced within the cylinder 14. The cylinder can be slidably mounted in a bearing 42. The front part of the cylinder and the front part of the bearing can form a valve 40, 44.

In a second operational state of the valve, the pump state, the valve member 44 can abut the valve seat 40, defining a stop position. An opening in the cylinder wall can overlap with the outlet conduit 25, while inlet conduit 24 can be sealingly closed by the cylinder wall. When the piston head 17 is pushed into the cylinder, as shown in FIG. 6(a), the liquid can be expelled through the outlet conduit 25, and further toward the downstream fluidic system (not shown).

In a first operational state of the valve, the refill state, as shown in FIG. 6(b), the cylinder 14 can be shifted in the bearing 42. The end of the cylinder can act as a stopper 47, abutting cams 46 of the bearing. In this first state, the outlet conduit can be sealingly closed by the cylinder wall, and the inlet conduit 24 can be connected to the cylinder through an opening in the cylinder wall. When the piston head 17 is retracted, liquid can flow from the primary reservoir (not shown) into the secondary reservoir of the cylinder.

The piston rod 18 can be provided with a scale 63 of optically distinguishable markings 64, 65, for example black and white fields, or reflective and not reflective fields. Both the cylinder and the bearing can be provided with windows 60, 62, which can be arranged such that they overlap when the valve is in the pump state. A light emitting device 56 can emit a light beam through the two windows to the scale 63 and a corresponding detector device 58 can detect the returning light signal. An evaluation unit 59 can determine an absolute position of the piston 16 within the cylinder 14 of the dosing unit and/or of a relative displacement of the piston within the cylinder based on the signal received from the the detector device 58. When the piston is pushed toward the cylinder end, the markings 64, 65 can pass the detector and can generate a number of signal flanks that can directly correspond to the relative displacement of the piston.

When the valve is in the refill state, the two windows 60, 62 may not overlap and the sensor 56 may not have access to the scale.

As for the embodiment in FIGS. 3, 4, 5, the valve switching can also be actuated by the piston, without the need for a separate valve actuator. However, in this embodiment, there can be no rotational movement of the piston or the cylinder. The friction between piston and cylinder can be higher than between cylinder and bearing. Thus if the valve is not in one of the two stop positions defining the two operational states, the piston can be frictionally coupled to the cylinder and a displacement of the piston can also move the cylinder in the bearing. When the valve reaches one of the two stop positions, the movement of the cylinder can be blocked and the piston can frictionally decoupled from the cylinder and can move within the cylinder.

In one embodiment of a dosing unit, the markings on the piston shaft can be replaced by through-holes, e.g., borings, that can radially cross the shaft and can allow the passage of a light beam emitted by a light emitting device through the shaft to a photosensor on the opposite side. In a further embodiment, the light emitter and the photosensor may be arranged on the same side and only reflecting elements can be provided on the opposite side that can reflect the light passing the through hole.

In another embodiment of a dosing unit, an absolute rotary or linear encoder can be used instead of the relative rotary or linear encoders. This can provide the possibility to omit the initializing of the position of the piston.

In a further embodiment, instead of optical markings, other suitably detectable markings may be used, e.g., conductive and non-conductive areas or magnetic and non-magnetic areas.

In an alternative embodiment, mechanical methods can be provided for encoding the rotation of the piston. For example, the piston may be provided with a multitude of teeth that can interact with a suitable resilient element e.g., on the cylinder, for example, a spring-biased pawl. Additional modulated friction can be added to the constant friction between piston and cylinder. As a result the force to be overcome during rotation of the piston and the necessary driving momentum of the motor can be also modulated, with the momentum modulation being reflected by a current modulation. The latter can be detected to determine the rotational position.

An additional feature of the detection system used to determine the rotation of the piston can be that it can also be used to check if during the pump modus the valve 35 is in the correct state. In the second state of the valve, as shown in the Figs, the window 60 can be used to detect the oscillating signal due to rotation of the piston. However, when the valve is switched, the window 60 can rotate together with the rest of the cylinder, thereby covering the markings 64, 65 from detection. Thus only if the valve is in the second state, the detection system 56, 58 can detect a signal when the piston is rotated. If no signal is detected when the valve is assumed to be in the second state and the drive unit is active, the control unit of the device can recognize an error event.

A dosing unit with windows that allow access to the encoder markings only in the discrete valve state positions, but not in the transient positions between, thus can be used to determine malfunctions or blockages of the valve.

In a further embodiment of such a dosing unit, a second window can be provided in the cylinder wall, which can provide optical access to the markings 64, 65 when the valve 35 is in the first state. This embodiment can have the additional advantage that also during the refill mode the displacement of the piston can be precisely controlled.

In yet another embodiment, the rotational position of the cylinder in regard to the static valve seat can be monitored by an independent detection system. For example may relative or absolute rotation encoder markings can be provided on the outer cylinder wall.

Before an infusion pump device can become operational, it may have to be properly prepared. Among other steps, the control and pump system may have to be initialized and the fluidic system may have to be filled with liquid medicament. This so called priming may be carried out if a pump unit is used for the first time or if the infusion tubing or disposable pump unit is replaced.

The accuracy of infusion pump devices in regard to dosing errors and administration of air bubbles can be considerably increased by filling the fluidic system of the infusion pump devices without air bubbles. This can mean that when the fluidic system, comprising the inlet conduit between primary reservoir and pump cylinder, the pump cylinder, the outlet conduit, and the connected infusion tubing can be filled with liquid for the first time prior to use, the introduction of air into the fluidic system should be avoided and air bubbles should be removed.

To prime the system in the known dosing units, the pump can be activated and can pump liquid medicament until the liquid reaches the end of the infusion tubing and the cannula attached to the tubing. The user can then stop the priming or the priming may stop automatically. The absence of air bubbles can be checked by a visual control of the tubing by the user. This priming procedure may not be cost efficient, since expensive liquid medicament may be unnecessarily wasted.

Furthermore, it can require a certain skill and understanding of the user which as a result can make the priming procedure error prone.

With an operation method for filling the fluidic system of an infusion pump device, the priming of a dosing unit with primary reservoir and secondary pump cylinder reservoir can be considerably improved. The method can be explained by referring to the schematically shown infusion pump device 10 in FIG. 2.

The infusion pump device 10 can comprise a primary reservoir 11 and a dosing unit 12 with a secondary reservoir 15 cylinder pump, having a cylinder 14, a bidirectionally displaceable piston 16, driven by a drive unit 20, and a 3/4 valve 35 for alternatingly connecting the pump cylinder to the inlet conduit 24 and the primary reservoir 11, and to the outlet conduit 25 and infusion tubing 28. Parts of the infusion pump device, advantageously the parts having direct contact with the liquid medicament, may be realized as disposable elements, while other parts can be realized as reusable parts. Alternatively, the complete pump device may be fully reusable or single use.

An air sensor 36 can be provided in the outlet conduit 25 downstream of the secondary reservoir 15 and can detect the presence of air in the conduit. Such an air sensor can for example be realized as an optical sensor, by measuring the transmission or reflection of light. In one embodiment, a light emitting element, e.g. an LED, can emit light through a suitable window in the conduit wall into the interior of the conduit. The illumination angle can be chosen such that if the conduit at the position of the sensor is filled with liquid, the light can enter the liquid and cross the conduit. If the conduit is empty (vacuum) or filled with air (air bubble), the light beam can be reflected on the boundary surface, and cannot cross the conduit. Either the light crossing the conduit, or the light reflected on the window/boundary surface, or both, can be detected by a suitable light detection element, e.g. a photo diode or a photo transistor.

Further downstream of the air sensor 36, an occlusion sensor 38 can be provided, which may, for example, be a pressure sensor. Such a pressure sensor can for example be realized with a micro-fluidic chamber where the pressure in the micro-fluidic chamber can be determined by measuring the deflection of a light beam by the surface of a flexible cover of the chamber.

The priming method can make use of the advantages of a dosing unit with a secondary reservoir cylinder pump and can prime the fluidic system based on the known volume of the fluidic system and the feedback of the air sensor and the occlusion sensor. The user can be relieved of most monitoring and handling tasks during the priming operation.

Figure 2:
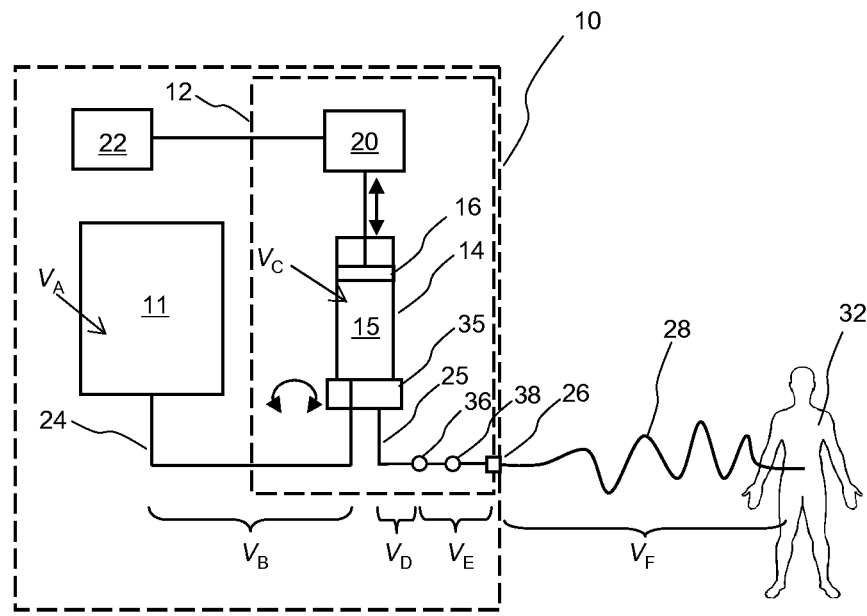
FIG. 2 illustrates schematically an infusion pump with a dosing unit of a downstream pump type with primary reservoir and secondary pump cylinder reservoir to which the priming method is applied according to an embodiment of the present disclosure.

The fluidic system of the infusion pump device 10 in FIG. 2 can comprise the volume $V_A$ of the primary reservoir; the volume $V_B$ of the fluidic system between primary 11 and secondary 15 reservoir, namely the volume of the inlet conduit 24 and any connectors, septums and the like present; the variable volume $V_C$ of the secondary reservoir; the volume $V_D$ of the fluidic system between secondary reservoir 15 and air sensor 36; the volume $V_E$ of the fluidic system between air sensor 36 and connector 26; and the volume $V_F$ of the infusion tubing 28.

Step A)

To efficiently and securely prime the dosing unit system, the volumes of the different parts of the fluidic system may need to be known. While the pump device can keep track on the current values of remaining liquid volume $V_A$ in the primary reservoir, as well as the current liquid volume $V_C$ in the secondary reservoir, the volumes $V_B$, $V_D$, $V_E$ can be given by the construction of the dosing unit, and can be provided predefined in a memory of a controller 22. Any dead volume of the secondary reservoir, that can mean the volume of the pump cylinder that cannot be emptied, can be considered to be a part of the downstream fluidic volume $V_D$.

The only volume that cannot be determined by the system itself may be the volume $V_F$ of the infusion tubing. Thus in a first step, the volume $V_F$ of the infusion tubing may need to be provided by the user. For that purpose, it can be sufficient to provide the length $L_F$ of predefined standard type tubing, which can have a known cross-sectional area $A_F$. The volume can be then given by $V_F = L_F * A_F$. The user may for example choose in a menu from a preselection of standard length infusion tubes provided for a particular pump system.

The current volume $V_A$ of the primary reservoir can be known to the system, since during infusion operation and priming operation, the amounts of liquid volume obtained from the reservoir can be continuously deducted from the reservoir volume. When a new, full primary reservoir is inserted into the infusion pump device, the current volume $V_A$ can be reset to the predefined start filling level $V_A=$ $V_{A, start}$ of that reservoir. This start volume may e.g. be recognized automatically, or may be entered by the user or may be determined with an additional filling level sensor.

The pump system can also keep track on the amount of air $V_{air}$ that has passed the air sensor in the fluidic system and thus can be present in the downstream fluidic system. This aspect of the disclosure will be discussed in more detail further below. Prior to the priming, $V_{air}$ can be reset to 0.

Step B)

The necessary liquid volume for the priming operation can be calculated. The volume for the priming of the upstream fluidic system can be $V_{Up}=V_B*SF_{Up}$, with $SF_{Up}$ being a safety factor, for example $SF_{Up}=1.0-1.5$. The volume for the priming of the downstream fluidic system can be $V_{Down}=(V_D+V_E V_F)*SF_{Down}$, with $SF_{Down}$ being a safety factor, for example $SF_{Down}=1.0-1.5$. If the required priming volumes exceed the remaining primary reservoir volume, $V_{Up}+V_{Down}>V_A$, an error message can be generated, requesting the user to replace the primary reservoir prior to initiating the priming.

Step C)

The priming operation can be initiated automatically by the system, or manually by the user. The piston 16 of the pump can be driven to the initial stop position in the cylinder. The filling level of the secondary reservoir 15 can be reset to $V_C=0$. For the steps as explained above, the valve 35 can be in the second state.

Step D)

The valve 35 can be set to the first state, in which the cylinder 14 can be connected with the primary reservoir 11. The controller 22 can cause the drive unit 20 to withdraw the piston 16 until the secondary reservoir volume is $V_C=V_{Up}$. The upstream part of the fluid system can now be primed with liquid medicament, while the secondary reservoir can be filled with liquid and an undefined amount of air from the upstream system. The primary reservoir volume can be updated to $V_A:=V_A-V_{Up}$.

If the priming is carried out for the first time after replacement of a disposable pump unit, the function of the air sensor 36 can be checked: If the air sensor determines air, the priming procedure can continue. If the air sensor detects liquid, an error message can be generated and the priming can be terminated.

Step E)

In a next step, the valve 35 can be set to the second state, in which the cylinder 14 can be connected with the outlet conduit 25. The piston can be driven to the initial position and any air and liquid medicament previously present in the pump cylinder can be expelled into the downstream fluidic system.

Step F)

The valve 35 can be set again to the first state where the cylinder 14 can be connected with the primary reservoir 1, and the piston can withdraw until the secondary reservoir volume is $V_C=V_{Down}$. The primary reservoir volume can be updated to $V_A:=V_A-V_{Down}$. The valve 35 can be set to the second state where the cylinder 14 can be connected with the outlet conduit 25, and the liquid medicament in the secondary reservoir 15 can be expelled into the downstream fluidic system, which can now also be primed with liquid medicament. The volume of the secondary reservoir can be now reset to $V_C=0$.

During the complete priming sequence, the occlusion sensor 38 can continuously monitor the pressure in the fluidic system and can trigger an occlusion alarm when the pressure exceeds a certain threshold value. The user may then be requested to check the infusion set.

During the priming of the downstream system, the air sensor 36 can continuously monitor the air into the downstream fluidic system, by determining the accumulated air volume $V_{air}$ in the downstream fluidic system:

$$V_{air,prime} = \int_{t_{active}}^{t_{end}} d_{air}s_{prime}\,dt,$$

with $s_{prime}$ being the pump rate during priming, for example defined in nl/min or IU/min. $d_{air}$ can be a detector function, with $d_{air}=1$ when the air detector detects air, and else $d_{air}=0$. $t_{start}$ can be the start of the downstream priming sequence. $t_{active}=t_{start}+V_D/s_{prime}$ can be the point in time when the air sensor 36 becomes fully operational, namely when the conduit section upstream of the air sensor with volume $V_D$ has been primed. $t_{end}$ can be the time at the end of the priming sequence of step F).

Step G)

If the accumulated air volume $V_{air,prime}$ remains below a certain predefined threshold value after finishing the downstream priming, the priming has been successfully completed. The user can be informed accordingly. If on the other hand, the accumulated air $V_{air,prime}$ exceeds the threshold value, the priming cannot be completed. The piston 16 can be driven back to its initial position, and steps D), E), F) can be repeated.

Step H)

If after several attempts, the priming cannot be successfully completed, or if the remaining liquid volume in the primary reservoir is not sufficient, the priming sequence can be terminated and the user can be informed accordingly with an error message. For example he may be requested to replace the disposable unit.

When the priming of the dosing unit has been successfully completed, the user can be informed accordingly. The user can connect the infusion tubing to the mounted infusion site interface and the infusion pump device can be operational.

The priming can also be repeated at a later time, for example, when the complete system is reinitialized for certain reasons. Advantageously, the user may interrupt an automatic priming procedure manually.

A possible fault condition that may occur during the normal operation of an infusion pump device can be the presence of an unknown amount of air in the dosing cylinder. Such an event may be the result of the primary reservoir being unexpectedly empty, or an occlusion or leakage in the upstream fluidic system. In the case of a leakage, air can be sucked in from the environment into the pump cylinder. In the case of an occlusion or an empty reservoir, a vacuum can be generated in the pump cylinder. When the pump valve is switched from refill mode to dosing mode, the cylinder may be aerated during the switching process.

During a dosing event, the pump can eventually convey the air that can be present in the cylinder into the downstream system. There it can be detected by the air sensor, which can generate a warning message and if necessary can interrupt the dosing. However, as long as the pump is not active, the air may not pass the air sensor and thus can remain undetected for a considerably time.

After an unwanted aeration of the pump cylinder, the inside of the cylinder can have environmental pressure. Due to a subsequent change in environmental temperature or pressure, a pressure differential can develop between the air locked in the pump cylinder and the environment. As a result liquid can be sucked in from the infusion tubing in the case of a negative pressure differential. When the pressure differential is positive, an unknown amount of liquid medicament can be conveyed in an uncontrolled manner into the infusion tubing, driven by the pressure differential, and eventually can be inadvertently administered to the patient.

The possible hazardous effect of such a dosing error can depends on the circumstances, particularly the type of medicament and the physiological condition of the patient. If the dosing error exceeds a certain level, the effects can be very dangerous. The value may differ considerably from patient to patient. For example, the same amount of insulin that may be still harmless for an adult person of 80 kg and low insulin sensitivity may be fatal for a child of 30 kg and high insulin sensitivity. Therefore, it can be a crucial requirement for a failsafe infusion pump device to avoid the inadvertent administration of a potentially fatal dose of liquid drug, even under the most unlikely circumstances.

In an operation method for metering doses of liquid medicament, this goal can be achieved by restricting the maximum refill level of the secondary reservoir during normal operation to a certain value. While this may lead to a larger number of pump refill events during continuous operation of the infusion pump device than theoretically necessary when always refilling the pump to its maximum level, a pressure/temperature change within certain pre-defined limits can lead to a reduced and improved dosing performance.

The unintentional pump effect that can lead to the discussed dosing errors can be given by the pressure differential between pump cylinder and environment, $\Delta p=(p_C-p_{env})$. A pressure differential may either result from a change of temperature T, or from a change of environmental pressure $p_{env}$. To maximize safety, one can consider parameter changes that may take place in real life even under unlikely circumstances. The environmental pressure may for example change within 10 min by 200 mbar, or even 500 mbar, in both directions. The temperature may change within 10 min by 10° C., or even 30° C., in both directions.

When the pressure differential is positive, the locked air with volume $V_{air,C,0}$ can expand to larger volume $V_{air,C,1}$ to equalize pressure, which can lead to a dosing error $V_{error}=(V_{air,C,1}-V_{air,C,0})$ of liquid that can be expelled. Due to the gas law pV=nRT, the dosing error can be directly proportional to the volume $V_{air,C,0}$ of air in the secondary reservoir, with $V_{error}=V_{air,C,0}$ ($\Delta T/T_0$), respectively $V_{error}=V_{air,C,0}$ ($\Delta p/p_1$). Since the amount of air in the cylinder is unknown, it can be for safety considerations preferable to use a hypothetical air volume $V_{air,C,max}=V_C$, corresponding to a hypothetical event where the complete cylinder can be filled with air. The above-given relation can be based on absolute values.

For operation of dosing unit, a worst-case acceptable dosing error for insulin may be defined, as an example, as about 5-20% of a total daily dose $V_{TDD}$ for a given individual patient. In such a case, the maximum refill level $V_{C,max}$ can for example be set to 20% of the total daily dose $V_{TDD}$. With such a value, the maximum possible dosing error that can result from short time fluctuations with high likelihood can be below 5% of the total daily dose $V_{TDD}$. If, as an example, during air plane travel the pressure drops from about 1000 mbar to 860 mbar, this would can correspond to a maximum possible dosing error of $V_{error,max}=V_{air,C}*16\% \leq V_C*16\% \leq V_{C,max}*16\% = V_{TDD}*3.25\%$. If, as an example, a patient leaves an air-conditioned room at 20° C. and walks onto the street at 40° C., this can result in a maximum possible dosing error due to the temperature increase of $V_{error,max} \leq V_{C,max}*7\% = V_{TDD}*1.4\%$. Even for a very unlikely events, for example a sudden cabin depressurization in an air plane, the maximum possible error can in no case be larger than $V_{error}=V_C$.

Thus by restricting the filling level of the secondary reservoir to a patient-dependent maximum level, it can be possible to adapt the operation of an infusion pump device to a particular patient ensuring a most safe operation for all users.

In one embodiment of the metering method, the method can be adapted to additional circumstances. For example, the maximum refill level $V_{C,max}$ can be temporarily reduced during air travel, thereby taking into account the possibility of a sudden pressure drop. For that purpose, the user may request the infusion pump device to enter a flight travel mode. Alternatively, the device can detect a slow drop of the environmental pressure, assuming that such a drop is due to the normal reduction of cabin pressure, and can switch to the flight mode automatically.

One advantage of the metering method can be the fact that also in the case of a failure event of the pump drive, where the pump drive does not stop to pump, the maximum amount of unintentionally infused medicine can be limited.

The refilling of the secondary reservoir may be required both during a bolus administration and at any other time during basal administration. The switching of the valve when the pump cylinder is refilled can inflict a certain small dosing error due to the shift of small amounts of volume. Although this error is very small, less than, for example, about 0.1 IU, it may nevertheless be relevant, for example, during the basal period of insulin administration. In one embodiment of a metering method, the dosing error can be minimized, by applying an advantageous refilling strategy for the pump. This kind of dosing error can be critical in so far as it can accumulate over time in dependence of the number of valve switching operations.

Figure 7:
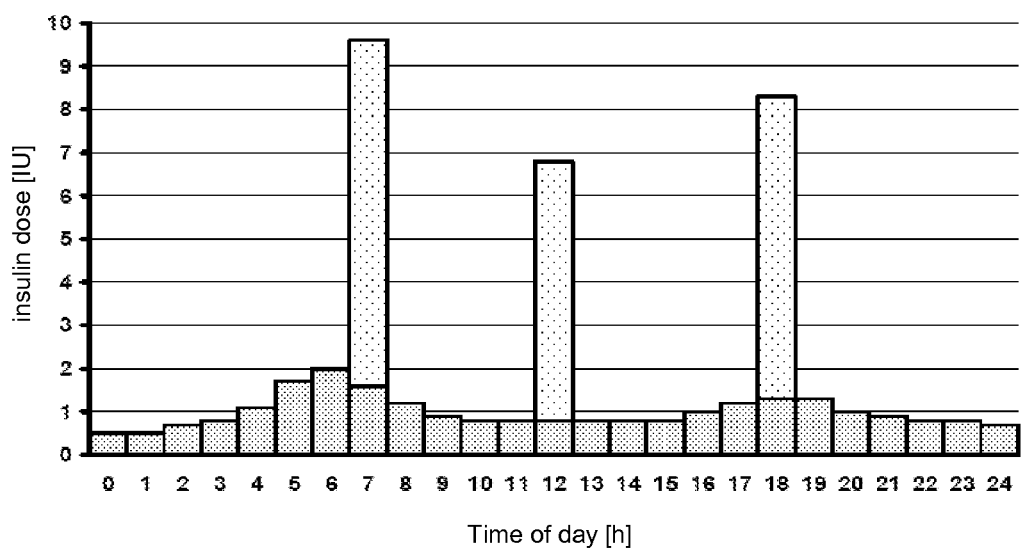
FIGS. 7a-d illustrate (a) a typical dosing profile for insulin when using an infusion pump device and (b), (c), (d) the accumulated insulin dose profile, together with the refill steps according to different pump refill strategies used in a dosing method according to an embodiment of the present disclosure.
Figure 7:
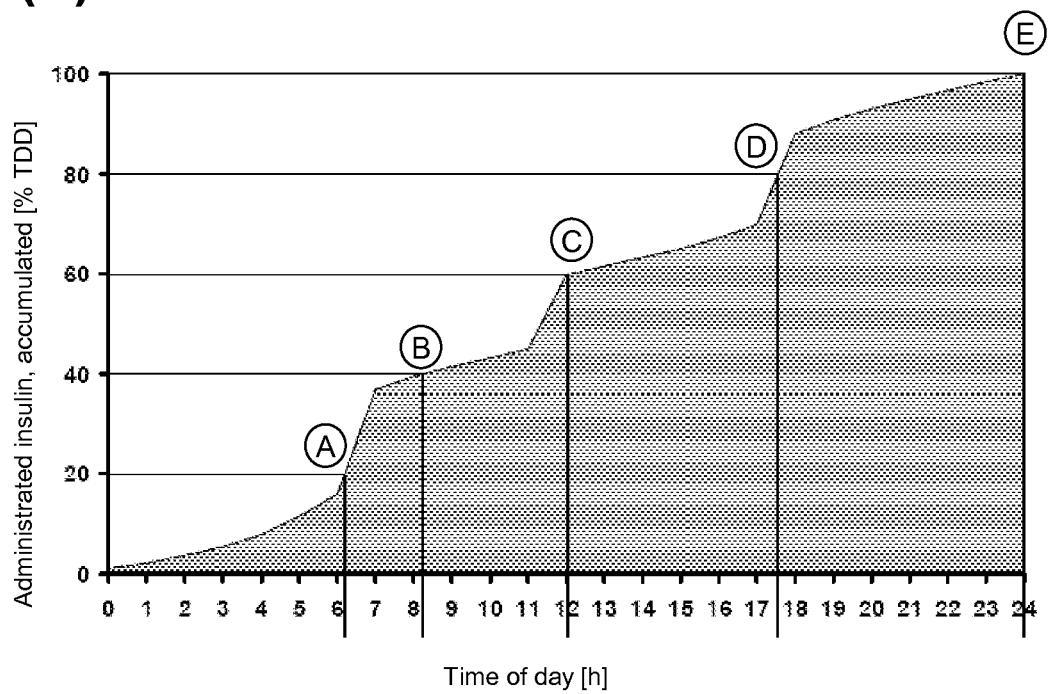
Figure 7:
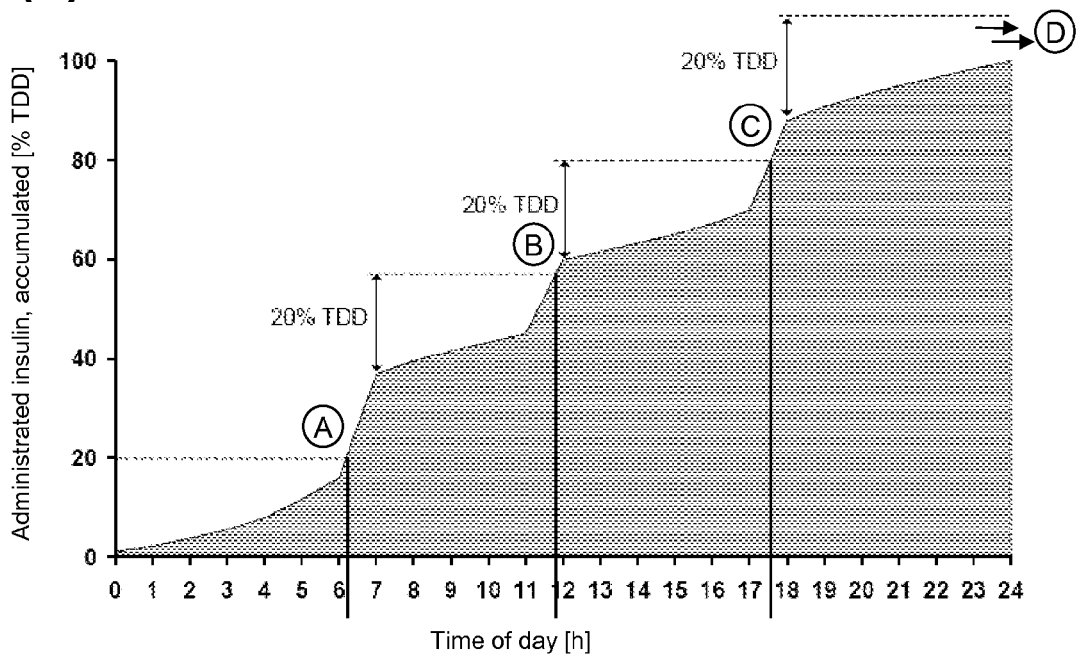
Figure 7:
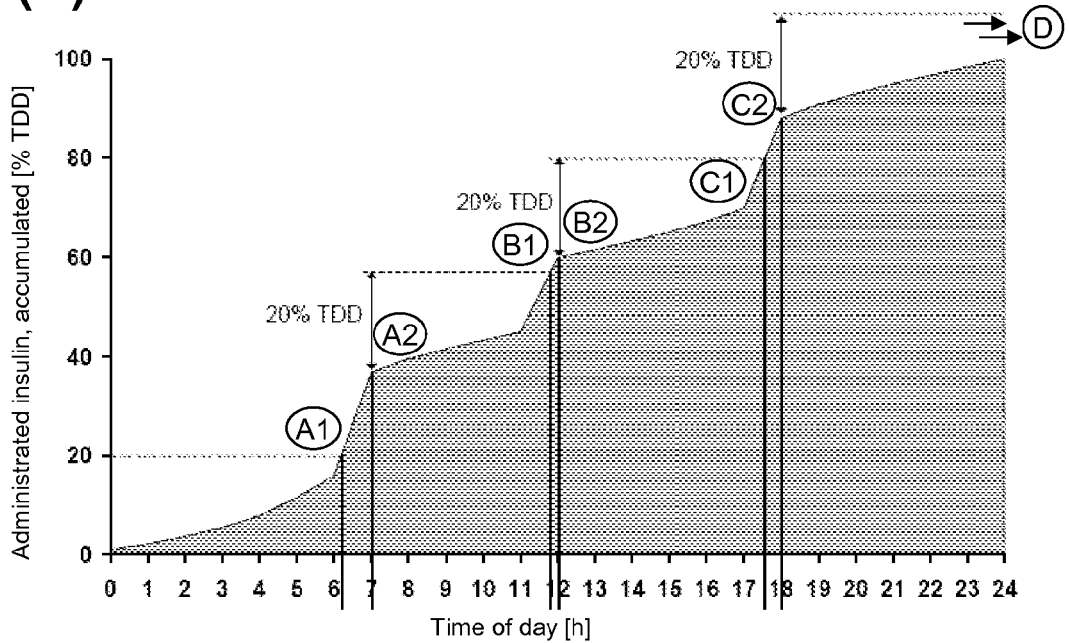

In one possible approach, the accumulated error can be minimized by minimizing the number of refilling steps during a certain period. This can be achieved by always refilling the pump to the maximum allowed value. This approach is explained by referring to FIG. 7, where (a) shows a simplified, typical insulin administration profile when using an infusion pump device, during a normal day. In addition to the administration of a basal dose on insulin (dark grey areas), covering the continuous need of the patient, three bolus doses (light grey) can be administered that take into account the increased need of insulin after the three meals. It can be noted that for a bolus administration the total bolus dose can be typically administered within a short time in the range of several seconds to several minutes. FIG. 7(b) shows the corresponding accumulated administered insulin dose, in percentages of the total daily dose TDD.

To minimize the number of refill steps, the secondary reservoir can be always completely emptied prior to refilling and can be also always completely refilled to the maximum refill level $V_{C,max}=V_{TDD}$. The maximum refill level can be, e.g., set to $V_{C,max}=V_{TDD}*20\%$ or, generally spoken, a certain percentage of the total daily dose $V_{TDD}$. Thus in the average only five refill steps may be necessary during a 24 hour period to cover the total daily dose in this example. The resulting refill steps can be marked by letters A to E. For patients for whom the maximum refill level $V_{C,max}$ exceeds design-given maximum refill level of the secondary reservoir, the latter may be used as refill level.

In another embodiment of a metering method, the number of refill steps can be further reduced. The method is explained by referring to FIG. 7(c). The strategy here is that in cases where the administration of a bolus requires a refilling of the pump cylinder, the refill volume may not be set to $V_{C,max}$, but can be calculated such that after complete administration of the bolus the remaining liquid medicament in the secondary reservoir can be equal to the allowed maximum refill level $V_{C,max}$. Thus the pump cylinder can be refilled to $V_{C,fill} = V_{rem.bolus} + V_{C,max} = V_{rem.bolus} \, V_{TDD}*20\%$, with $V_{rem.bolus}$ being the remaining bolus volume that still can be administered when the refilling becomes necessary.

Obviously after refilling the pump, the filling level can be above the maximum refill level. However, immediately afterwards the volume can be reduced again to the maximum refill level by expelling the remaining bolus volume $V_{rem.bolus}$. Thus the refill volume can be increased without increasing a possible dosing error, since the surplus filling volume can be administered immediately anyway. In addition, in the case of a fault condition causing an unwanted aeration of the secondary reservoir, this can be immediately detected by the air sensor. As a result, the number of refill steps can be further reduced, while the safety level can remain the same. In the shown example, approximately four refill steps A, B, C, D may be necessary per day.

In a further embodiment of a metering method, not the absolute number of refill steps but the number of refill steps during basal administration periods, that is, between typically meal-related bolus administrations, can be minimized, as shown in FIG. 7(d). If the secondary reservoir has to be refilled during a bolus administration, the cylinder can be only refilled with the remaining volume $V_{rem.bolus}$ of the bolus. At the end of the bolus administration, the pump cylinder can be empty and can be refilled to the maximum refill level $V_{C,max}$. Thus effectively every refill step during a bolus can be divided into two refill steps. This strategy can make use of the fact that during a bolus a small dosing error due to the refilling can be masked by the physiological effects of the much larger bolus dose. Thus the increased amount of refill steps can be less critical. During basal periods with its much smaller doses, however, where a dosing error can have more effect, the number of refill steps can be minimized.

In some embodiments, the secondary reservoir can be filled to the maximum refill level $V_{C,max}$ following every bolus administration, or every bolus administration beyond a predefined bolus volume threshold, even if the total bolus volume can be administered without refilling of the secondary reservoir and the secondary reservoir can be still partly filled after the bolus administration. In this way, it can be ensured that the volume corresponding to the maximum refill level can always be available for subsequent basal administration.

In the above mentioned methods, the secondary reservoir can be typically completely emptied prior to refilling. It can also be possible to refill the secondary reservoir while still containing liquid medicament, for example prior to a bolus such that the secondary reservoir can be filled to the maximum refill level $V_{c,max}$ after the bolus administration. However, completely emptying the pump can have the advantage that no volume or piston position errors can be accumulated. Furthermore, no air can accumulate in the cylinder, and if air is present, it can be expelled into the downstream system, where it can be detected by the air sensor.

Air sensors as known in the prior art can only distinguish between "air" and "no air" at the point of detection. In an infusion pump device, the air sensor cannot only be used to detect the presence of air. In addition, the amount of air in the complete downstream fluidic system can be continuously monitored.

For this purpose, the device can record all single administration events (which can be identified by a sequential number "i"), where the pump can be active and liquid medicament can be administered within a certain time period, e.g., 24 h, comprising the time of administration $t_i$ (begin of the activation of the pump), the nominally administered volume of liquid medicament $V_{dose,i}$, and the detected amount $V_{air,i}$ of air. The amount can be determined by accumulating the time $t_{air,i}$ during administration when the air detector can detect air in the fluidic system: $V_{air,i} = t_{air,i} \, s_{dose}$, with $s_{dose}$ being the pump rate during administration.

The system can continuously calculate a rolling integral over the detected volumes of air. If the amount of air that has passed the sensor within a certain time period exceeds a certain threshold value, an error message can be generated, requesting the user to take the appropriate action. In one embodiment, different threshold values for different accumulation periods can be applied.

The recordation of the data may for example be realized as a FIFO (First-In-First-Out) register of sufficient length in a memory unit of the controller 22, as shown in FIG. 8, into which the data sets are entered. In FIG. 8, $t_{admin,i}$ can signify the time period from the begin $t_i$ of the activation of the pump to the begin $t_{i+1}$ of the next activation of the pump. $V_{dose,i}$ can be the volume of liquid medicament nominally administered during that period by the dosing unit. It can be given in millimeters of the used infusion tubing length, but may also be given in nanoliters, cubic millimeters, insulin units and the like. The detected air volume $V_{air,i}$ can be given in insulin units, but may also be expressed in further volume units, such as micro-liters. Also here other convenient units may be applied. In the given example, two different basal rates can be applied during a day, and the administration of one bolus is shown.

A new data set can be entered at the top of the register, while the oldest data set can fall out at the bottom of the registry. The length of the register can be chosen such that it i can be sufficient to store at least data for the longest integration period.

In the given example, two accumulated air volumes $V_{air,24h}$, $V_{air,Down}$ can continuously be calculated and monitored. For air volume $V_{air,24h}$ the data entries for the last 24 hours can be assessed:

$$V_{air,24h} = \sum_{i=1}^{n} V_{air,i}$$

with n being chosen such that $$\sum_{i=1}^{n} t_{admin,i} \approx 24 \text{ h}.$$

Instead of a time period of 24 h, any other suitable time period may be applied, for example 12 h or 48 h. The value n may change when variable administration periods are applied. Each time a new data set is entered in the FIFO, the accumulated air volume can be recalculated.

$V_{air,24h}$ can correspond to the air volume that has passed the air sensor within a period of 24 h. If this value exceeds a certain threshold value, $V_{air,24h} > V_{air,max,24h}$, a corresponding alarm can be triggered so that the necessary actions can be taken. By monitoring $V_{air,24h}$, the infusion pump device can monitor the amount of air that is administered to the patient. At the same time this value can represent also an accumulated dosing error due to the air, since the actually administered liquid medicament can be smaller than the nominal administered dose: $V_{dose,real,24h}=V_{dose,24h}-V_{air,24h}$. Furthermore, the correct long time function of the fluidic system can be monitored, since leakage that appears only after the priming procedure can be detected.

The second monitored air volume $V_{air,Down}$ can comprise the data entries that can correspond to a dosing volume that can be equal to the fluidic system volume downstream of the air sensor, $V_{Down}=V_E+V_F$, thereby representing the amount of air currently present in the downstream system, but not yet administered to the patient:

$$V_{air,Down} = \sum_{i=1}^{m} V_{air,i},$$

with m being chosen such that $$\sum_{i=1}^{m} V_{dose,i} \approx V_{Down}.$$

Again, each time a new data set is entered in the FIFO, the accumulated air volume can be recalculated. If the value exceeds a certain threshold value, $V_{air,Down}>V_{air,max,Down}$, an alarm can be triggered so that the necessary actions can be taken. By monitoring $V_{air,Down}$ the infusion pump device can monitor the amount of air that can be administered to the patient if operation continues. Furthermore, this value can also be related to a potential dosing error in case of a pressure or temperature change, since in such a case the air in the downstream system can expand, and liquid can be inadvertently administered. $V_{air,Down}$ can also be used to monitor the correct operation of the pump device and to detect leakages.

Alternatively or in addition, the amount of detected air may also be monitored in relation to the administered volume of liquid medicament. For example, the infusion pump device may monitor if the relation $V_{air,24h}/V_{dose,24h}$ between air and liquid medicament does not exceed a certain threshold value.

In one embodiment, the amount of air administered to the patient can be determined very exactly by the approach shown in FIG. 9. The accumulation range for 24 hours and for the downstream system cannot be overlapping, as discussed above, but can be arranged in sequence:

$$V_{air,Down} = \sum_{i=1}^{m} V_{air,i},$$

with m being chosen such that $$\sum_{i=1}^{m} V_{dose,i} \approx V_{Down},$$

and $$V'_{air,24h} = \sum_{i=m+1}^{k} V_{air,i}$$

with k being chosen such that $$\sum_{i=m+1}^{k} t_{admin,i} \approx 24 \text{ h}.$$

Again $V_{air,Down}$ describes the air in the downstream system, while $V'_{air,24h}$ describes the amount of air that has actually left the infusion tubing and has been administered to the patient within a period of 24 h.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A dosing unit for an ambulatory infusion pump device, the dosing unit comprises:
    a cylinder pump comprising,
        a cylinder; and
        a piston displaceable along a longitudinal axis of the cylinder, wherein the piston has a piston head and a piston shaft, wherein the piston shaft has a shaft segment provided with markings that can be detected, and wherein the markings are a plurality of stripes arranged on the shaft segment in the form of at least two stripes arranged on the shaft segment along the circumference of the shaft and parallel to the longitudinal axis;
    a valve that can be in two operational states; and
    a window provided on the cylinder for providing optical access to the plurality of stripes, wherein the window provides optical access to the plurality of stripes when the valve is in one of the two operational states and does not provide optical access to the plurality of stripes when the valve is between the two operational states.

2. The dosing unit according to claim 1, wherein the markings are optically detectable stripes.

3. The dosing unit according to claim 1, wherein the piston shaft comprises a threaded segment interacting with a threaded portion of the cylinder in such a way that the piston is displaced along the longitudinal axis when the piston shaft is rotated around the axis.

4. The dosing unit according to claim 3, wherein the shaft segment is between a first threaded segment and the piston head.

5. An infusion pump device with the dosing unit according to claim 1.

6. The infusion pump device according to claim 5, further comprising,
    one or more sensor units to detect the markings of the piston of the dosing unit mounted in the infusion pump device; and an evaluation unit that based on a signal received from the one or more sensor units determines an absolute position of the piston within the cylinder of the dosing unit and/or of a relative displacement of the piston within the cylinder.

7. The infusion pump device according to claim 6, wherein the markings of the piston of the dosing unit mounted in the infusion pump device are optical markings and that the dosing unit comprises a valve that can be in two operational states, and a window on the cylinder allowing optical access to the optical markings of the piston, wherein the optical access window and the one or more sensor units of the infusion pump device are arranged in such a way that the one or more sensor units have optical access to the optical markings when the valve is in one of the two operational states and have no optical access to the optical markings when the valve is between the two operational states.

8. A kit comprising an infusion pump device and one or more dosing units according to claim 1.

9. A dosing unit for an ambulatory infusion pump device, the dosing unit comprises:
- a cylinder pump comprising
  - a cylinder; and
  - a piston displaceable along a longitudinal axis of the cylinder, wherein the piston has a piston head and a piston shaft, wherein the piston shaft has a segment provided with markings that can be detected, and wherein the markings are a plurality of stripes arranged on the shaft segment;
- a valve that can be in two operational states; and
- a window provided on the cylinder for providing optical access to the plurality of stripes,
- wherein the window provides optical access to the plurality of stripes when the valve is in one of the two operational states and does not provide optical access to the plurality of stripes when the valve is between the two operational states.

10. A dosing unit for an ambulatory infusion pump device, the dosing unit comprises:
- a cylinder pump comprising,
  - a cylinder; and
  - a piston displaceable along a longitudinal axis of the cylinder, wherein the piston has optically detectable markings allowing for the determination of an absolute position of the piston within the cylinder and/or of a relative displacement within the cylinder;
- a valve that can be in two operational states; and
- a window on the cylinder for providing optical access to the optically detectable markings, wherein the optical access window provides optical access to the optically detectable markings when the valve is in one of the two operational states and does not provide optical access to the optically detectable markings when the valve is between the two operational states.

11. The dosing unit according to claim 10, wherein a piston shaft of the piston has a marker segment on which the optical markings are provided in the form of at least two stripes arranged on a second shaft segment along the circumference of the piston shaft and parallel to the longitudinal axis.

12. The dosing unit according to claim 10, wherein a piston shaft of the piston has a marker segment on which the optical markings are provided in the form of a plurality of optically circumferential rings arranged on a second shaft segment.

13. The dosing unit according to claim 10, wherein the piston comprises a piston head and a piston shaft with a threaded segment interacting with a threaded portion of the cylinder in such a way that the piston is displaced along the longitudinal axis when the piston shaft is rotated around the axis.

14. The dosing unit according to claim 13, wherein a second marker segment is between the first threaded segment and the piston head.

15. The dosing unit according to claim 10, wherein the valve for alternatingly connecting an inner volume of the cylinder in a first operation state to an inlet conduit and in a second operational state to an outlet conduit comprising a valve seat and a valve member, wherein the valve member is part of the cylinder, and wherein the cylinder is rotatably or slidably mounted in a bearing of the valve seat such that the valve can be switched between the two states by rotating the cylinder with the valve member by a certain angle along the longitudinal axis of the cylinder, or by displacing the cylinder with the valve member in regard to the valve seat by a certain distance along the longitudinal axis.

* * * * *